US011419836B2

(12) United States Patent
Millet

(10) Patent No.: US 11,419,836 B2
(45) Date of Patent: *Aug. 23, 2022

(54) RACEMIC AND NEAR RACEMIC BETA-HYDROXYBUTYRATE MIXED SALT-ACID COMPOSITIONS

(71) Applicant: AXCESS GLOBAL SCIENCES, LLC, Salt Lake City, UT (US)

(72) Inventor: Gary Millet, Salt Lake City, UT (US)

(73) Assignee: AXCESS GLOBAL SCIENCES, LLC, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/190,062

(22) Filed: Mar. 2, 2021

(65) Prior Publication Data

US 2021/0177786 A1 Jun. 17, 2021

Related U.S. Application Data

(63) Continuation-in-part of application No. 16/783,956, filed on Feb. 6, 2020, now Pat. No. 10,973,792.

(60) Provisional application No. 62/805,054, filed on Feb. 13, 2019.

(51) Int. Cl.
  *A61K 31/19* (2006.01)
  *A61K 45/06* (2006.01)

(52) U.S. Cl.
  CPC .............. *A61K 31/19* (2013.01); *A61K 45/06* (2013.01)

(58) Field of Classification Search
  CPC .............................. A61K 31/19; A61K 45/06
  See application file for complete search history.

(56) References Cited

U.S. PATENT DOCUMENTS

| | | |
|---|---|---|
| 2,238,149 A | 4/1941 | Aeckerle |
| 2,976,073 A | 3/1961 | Russell et al. |
| 4,627,808 A | 12/1986 | Hughes |
| 4,997,976 A | 3/1991 | Brunengraber et al. |
| 5,093,044 A | 3/1992 | Wretlind et al. |
| 5,116,868 A | 5/1992 | Chen et al. |
| 5,288,512 A | 2/1994 | Seiden |
| 5,292,774 A | 3/1994 | Hiraide et al. |
| 5,654,266 A | 8/1997 | Chen et al. |
| 5,700,670 A | 12/1997 | Yamagishi et al. |
| 6,207,856 B1 | 3/2001 | Veech |
| 6,217,915 B1 | 4/2001 | Luchansky et al. |
| 6,316,038 B1 | 11/2001 | Veech |
| 6,323,237 B1 | 11/2001 | Veech |
| 6,380,244 B2 | 4/2002 | Martin et al. |
| 6,613,356 B1 | 9/2003 | Vlahakos |
| 6,706,756 B1 | 3/2004 | Fitzpatrick et al. |
| 6,835,750 B1 | 12/2004 | Henderson |
| 7,351,736 B2 | 4/2008 | Veech |
| 7,807,718 B2 | 10/2010 | Hashim et al. |
| 8,101,653 B2 | 1/2012 | Veech |
| 8,124,589 B2 | 2/2012 | Henderson |
| 8,426,468 B2 | 4/2013 | Henderson |
| 8,642,654 B2 | 2/2014 | Clarke et al. |
| 8,748,400 B2 | 6/2014 | Henderson |
| 9,138,420 B2 | 9/2015 | D'Agostino et al. |
| 9,211,275 B2 | 12/2015 | Clarke et al. |
| 9,675,577 B2 | 6/2017 | D'Agostino et al. |
| 9,717,767 B2 | 8/2017 | Carpenter et al. |
| 9,795,580 B2 | 10/2017 | Weeber et al. |
| 9,808,481 B2 | 11/2017 | Ritter et al. |
| 9,957,246 B2 | 5/2018 | Stinchcomb et al. |
| 10,022,409 B2 | 7/2018 | Carpenter et al. |
| 10,051,880 B2 | 8/2018 | Clarke et al. |
| 10,245,242 B1 | 4/2019 | Millet |
| 10,245,243 B1 | 4/2019 | Millet |

(Continued)

FOREIGN PATENT DOCUMENTS

| | | |
|---|---|---|
| CN | 1347319 A | 5/2002 |
| EP | 2283834 A2 | 2/2011 |

(Continued)

OTHER PUBLICATIONS

A New Toy Measuring Blood Ketones. Diet Doctor, Aug. 21, 2012. Downloaded Apr. 1, 2015. http://www.dietdoctor.com/a-new-toy-measuring-blood-ketoones.
Arendash et al. "Caffeine and Coffee as Therapeutics Against Alzheimer's Disease", Journal of Alzheimer's Disease 20, 2010, S117-S126.
Arnold, Instant Ketosis?, (2013), Aug. 4, 2013 (retrieved on Apr. 21, 2017), p. 1-3 Retrieved from the internet; URL: <http://patrickarnoldblog.com/instant-ketosis/. (Year: 2013).
Bastin et al., "Salt Slection and Optimisation Procedures for Pharmaceutical New Chemical Entities", American Chemical Society and The Royal Society of Chemistry, vol. 4, No. 5, 2000, pp. 427-435.
Clarke, et al., Kinetics, safety and tolerability of (R)-3-hydroxybutyl (R)-3-hydroxybutyrate in healthy adult subjects. Regul Toxicol Pharmacol. Aug. 2012;63(3):401-8.

(Continued)

*Primary Examiner* — Sahar Javanmard
(74) *Attorney, Agent, or Firm* — Workman Nydegger

(57) ABSTRACT

Ketogenic compositions include a racemic or near racemic mixture of R- and S-beta-hydroxybutyric acids and a racemic or near racemic mixture of R- and S-beta-hydroxybutyrate salts. The R-enantiomer elevates ketone bodies and increases the rate at which ketosis is achieved. Including an equivalent or near equivalent amount of the S-enantiomer to provide alternative benefits. The R- and S-beta-hydroxybutyric acids are more rapidly absorbed and utilized by the body than salts or esters, enhance taste, and reduce the need to include other edible acids. The R- and S-beta-hydroxybutyrate salts are more slowly absorbed and utilized by the body and can provide one or more electrolytes. The composition may contain a dietetically or pharmaceutically acceptable carrier and a racemic or near racemic mixture of R- and S-beta-hydroxybutyrate salts and acids. The composition contains <100% by molar equivalents of total R,S-beta-hydroxybutyrate salts and >0% by molar equivalents of R,S-beta-hydroxybutyric acids.

20 Claims, 2 Drawing Sheets

(56) References Cited

U.S. PATENT DOCUMENTS

| | | | |
|---|---|---|---|
| 10,292,592 | B2 | 5/2019 | Marshall et al. |
| 10,292,952 | B2 | 5/2019 | Millet |
| 10,512,615 | B1 | 12/2019 | Millet |
| 10,588,877 | B2 | 3/2020 | Arnold |
| 10,596,128 | B2 | 3/2020 | Millet |
| 10,596,130 | B2 | 3/2020 | Millet |
| 10,660,958 | B2 | 5/2020 | Clarke |
| 10,736,861 | B2 | 8/2020 | Millet |
| 10,925,843 | B2 | 2/2021 | Millet |
| 11,020,362 | B2 | 6/2021 | Millet |
| 2001/0014696 | A1 | 8/2001 | Veech |
| 2001/0041736 | A1 | 11/2001 | Veech |
| 2003/0022937 | A1 | 1/2003 | Veech |
| 2004/0266872 | A1 | 12/2004 | Veech |
| 2005/0129783 | A1 | 6/2005 | McCleary et al. |
| 2007/0179197 | A1 | 8/2007 | Henderson |
| 2008/0058416 | A1 | 3/2008 | Greenwood et al. |
| 2008/0287372 | A1 | 11/2008 | Henderson |
| 2009/0253781 | A1 | 10/2009 | Veech |
| 2010/0041751 | A1 | 2/2010 | Henderson |
| 2010/0056631 | A1 | 3/2010 | Hisamura et al. |
| 2010/0197758 | A1 | 8/2010 | Andrews et al. |
| 2010/0298294 | A1 | 11/2010 | Clarke et al. |
| 2011/0237666 | A1 | 9/2011 | Clarke et al. |
| 2012/0053240 | A1 | 3/2012 | Rathmacher et al. |
| 2012/0071548 | A1 | 3/2012 | Veech |
| 2012/0202891 | A1 | 8/2012 | Stinchcomb et al. |
| 2013/0079406 | A1 | 3/2013 | Veech |
| 2013/0337116 | A1 | 12/2013 | Petralia |
| 2015/0065571 | A1 | 3/2015 | Clarke et al. |
| 2015/0132280 | A1 | 5/2015 | Lopez et al. |
| 2016/0193173 | A1 | 7/2016 | Clarke et al. |
| 2016/0256411 | A1 | 9/2016 | Aung-Din |
| 2017/0020844 | A1 | 1/2017 | Galinski |
| 2017/0172969 | A1 | 6/2017 | D'Agostino et al. |
| 2017/0258745 | A1 | 9/2017 | Millet |
| 2017/0266148 | A1 | 9/2017 | D'Agostino et al. |
| 2017/0290792 | A1 | 10/2017 | Cavaleri |
| 2017/0296501 | A1 | 10/2017 | Lowery et al. |
| 2017/0298339 | A1 | 10/2017 | Hanson et al. |
| 2017/0304564 | A1 | 10/2017 | Dehaan et al. |
| 2018/0021274 | A1* | 1/2018 | Arnold ............... A61K 9/08 514/557 |
| 2018/0055797 | A1 | 3/2018 | Llosa et al. |
| 2018/0057846 | A1 | 3/2018 | Llosa et al. |
| 2018/0195096 | A1 | 7/2018 | Veech et al. |
| 2019/0099394 | A1 | 4/2019 | Ari et al. |
| 2019/0167613 | A1 | 6/2019 | Millet |
| 2019/0183820 | A1 | 6/2019 | Millet |
| 2019/0191755 | A1 | 6/2019 | Garvey et al. |
| 2019/0209501 | A1 | 7/2019 | Tinsley et al. |
| 2019/0313682 | A1 | 10/2019 | Nagel |
| 2020/0078973 | A1 | 3/2020 | Bruno et al. |
| 2020/0140371 | A1 | 5/2020 | Verdin et al. |

FOREIGN PATENT DOCUMENTS

| | | | |
|---|---|---|---|
| EP | 2976073 | A1 | 1/2016 |
| EP | 3094321 | A1 | 11/2016 |
| JP | 11-060434 | A | 3/1999 |
| JP | 2002-521330 | A | 7/2002 |
| JP | 2015-042644 | A | 3/2015 |
| JP | 2015-514104 | A | 5/2015 |
| JP | 2016-514725 | A | 5/2016 |
| JP | 2017-046688 | A | 3/2017 |
| JP | 2020-502652 | A | 1/2020 |
| JP | 2020-527583 | A | 9/2020 |
| JP | 2021-504476 | A | 2/2021 |
| JP | 2021-506294 | A | 2/2021 |
| RU | 2345546 | C2 | 2/2009 |
| WO | 87/03808 | A1 | 7/1987 |
| WO | 98/41200 | A1 | 9/1998 |
| WO | 03/70823 | A2 | 8/2003 |
| WO | 2005/107724 | A1 | 11/2005 |
| WO | 2007/115282 | A2 | 10/2007 |
| WO | 2008/005818 | A1 | 1/2008 |
| WO | 2008/021394 | A2 | 2/2008 |
| WO | 2008/024408 | A2 | 2/2008 |
| WO | 2011/101171 | A1 | 8/2011 |
| WO | 2013/150153 | A1 | 10/2013 |
| WO | 2014/153416 | A1 | 9/2014 |
| WO | 2015/071811 | A1 | 5/2015 |
| WO | 2015/156865 | A1 | 10/2015 |
| WO | 2016/123229 | A1 | 8/2016 |
| WO | 2017/156446 | A1 | 9/2017 |
| WO | 2017/165443 | A1 | 9/2017 |
| WO | 2017/165445 | A1 | 9/2017 |
| WO | 2017/208217 | A2 | 12/2017 |
| WO | 2018/055388 | A1 | 3/2018 |
| WO | 2018/089863 | A1 | 5/2018 |
| WO | 2019/018683 | A1 | 1/2019 |
| WO | 2019/204148 | A1 | 10/2019 |
| WO | 2019/237152 | A1 | 12/2019 |

OTHER PUBLICATIONS

Dietary Guidelines Recommendations at https://health.gov/our-work/food-nutrition/2015-2020-dietary-guidelines/guidelines/ appendix-7/ (2010) (retrieved from the internet Oct. 20, 2020) (Year: 2010).

Dolson, Laura. How to Test Your Blood for Ketones. Downloaded Apr. 1, 2015. http://lowcarbdiets.about.eom/od/KetogenicDiets/a/How-to-Test-Blood-For-Ketones.htm.

Extended European Search Report issued in PCT/US2017021886 dated Oct. 17, 2019.

First Examination Report for New Zealand Patent Application No. 711433 issued by the New Zealand Intellectual Property Office dated Mar. 10, 2016.

First Office Action issued by the Chinese State Intellectual Property Office dated Nov. 4, 2016 for corresponding Chinese Patent Application No. 201480016818.0.

Hashim, Sarni A., et al., "Ketone body therapy: from the ketogenic diet to the oral administration of ketone ester", Journal of Lipid Research, vol. 55, 2014.

Haywood A, Glass BD. Pharmaceutical excipients—where do we begin? Australian Prescriber. 2011; 34: 112-114.

Henderson, Samuel T. "Ketone Bodies as a Therapeutic for Alzheimer's Disease." Neurotherapeutics. Jul. 2008;5(3):470-80.

Holtzman et al., "Role of adenosine receptors in caffeine tolerance", J. Pharmacol. Exp. Ther., 1991 ;256(1 ):62-68.

International Preliminary Reporton Patentability received for PCT Patent Application No. PCT/US2019/048364, dated Mar. 11, 2021, 7 pages.

International Search Report and Written Opinion issued in PCT/US19/48357 dated Nov. 18, 2019.

International Search Report and Written Opinion issued in PCT/US19/48364 dated Nov. 15, 2019.

International Search Report and Written Opinion issued in PCT/US20/16952 dated Apr. 22, 2020.

International Search Report and Written Opinion issued in PCT/US20/17552 dated May 4, 2020.

International Search Report and Written Opinion issued in PCT/US20/17555 dated May 4, 2020.

International Search Report and Written Opinion issued in PCT/US20/17556 dated May 4, 2020.

International Search Report and Written Opinion received for PCT Patent Application No. PCT/US20/37289, dated Sep. 30, 2020, 8 pages.

International Search Report and Written Opinion received for PCT Patent Application No. PCT/US2020/033159, dated Aug. 12, 2020, 9 pages.

International Search Report and Written Opinion received for PCT Patent Application No. PCT/US21/17078, dated Apr. 23, 2021, 9 pages.

International Search Report cited in PCT/US18/62093 dated Feb. 1, 2019.

International Search Report cited in PCT/US19/27214 dated Jun. 25, 2019.

(56) References Cited

OTHER PUBLICATIONS

It Really is in Your Blood: Glucose to Ketone Ratios. Greymadder, Sep. 15, 2014. Downloaded Apr. 1, 2015. http://greymadder.net/2014/09/15/it-really-is-in-your-blood-glucose-to-ketone-ratios/.

James, "Optical Purity and Enantiomeric Excess" at https://www.masterorganicchemistry.com/2017/02/24/optical-purity-and-enantiomeric-excess/. (Retrieved from the internet Nov. 6, 2018) (Year: 2018).

Karppanen et al, J. Human Hypertension (2005), vol. 19, pp. S10-S19. (Year: 2005).

Kesl, et al., "Effects of exogenous ketone supplementation on blood ketone, glucose, triglyceride, and lipoprotein Tevels in Spraque-Dawley rats", Nutrition & Metabolism (2016).

Kirsch, Jretal. "Butanediol Induced Ketosis Increases Tolerance to Hypoxia in the Mouse." Stroke. 1980, vol. 11, No. 3, pp. 506-513.

Kossoff, Eric H. et al. "Optimal Clinical Management of Children Receiving the Ketogenic Diet: Recommendations of the International Ketogenic Diet Study Group." Epilepsia, Feb. 2009;50(2):304-17. Epub Sep. 23, 2008.

Krotkiewski, "Value of VLCD Supplementation with Medium Chain Triglycerides", Int J Obes Relat Metab Disord, Sep. 2001, 25(9), pp. 1393-1400.

Murray, Andrew J., et al. "Novel ketone diet enhances physical and cognitive performance", The FASEB Journal, Vo. Dec. 30, 2016.

Nova Max Plus Glucose and Ketone Testing with One Monitor. Downloaded Apr. 1, 2015. http://www.novacares.com/nova-max-plus/.

Parker, Steve, "Ketogenic Mediterranean Diet: Version 2.3," Nov. 23, 2010, pp. 1-3. (Year: 2010).

PCT International Search Report and Written Opinion issued by the International Searching Authority dated Jul. 15, 2014 or International Patent Application No. PCT/US2014/031237.

Precision Xtra vs. NovaMax Plus: Ketone Meter Evaluation. Jimmy Moore's Livin' La Vida Low Garb Blog. Downloaded Apr. 1, 2015. http://livinlavidalowcarb.com/blog/precision-xtra-vs-novamax-plus-ketone-meter-evaluation/15918.

Pubchem, "Acetoacetic acid" Electronic Resource: https://pubchem.ncbi.nim.nih.gov/compound/Acetoacetic-acid, Retrieved on Sep. 3, 2019.

Requirement for Restriction/Election received for U.S. Appl. No. 16/551,570, dated Sep. 28, 2020, 6 pages.

Robson et al. Expert Opin. Drug Saf. (2011), vol. 10, pp. 675-685 (Year: 2011).

Roeder, Lois M., et al. The Effects of Ketone Bodies, Bicarbonate, and Calcium on Hepatic Mitochondrial Ketogenesis. Archives of Biochemistry and Biophysics, vol. 217, No. 2, Sep. pp. 460-467, 1982.

Sajewicz et al. In Journal of Liquid Chromatography & Related Technologies, 33:1047-1057 (2010) (Year: 2010).

Serum Ketones Test. MedlinePlus Medical Encyclopedia. Downloaded Apr. 1, 2015. http://www.nlm.nih.gov/medlineplus/ency/article/003498.htm.

Shigeno etal. In Biosci. Biotech. Biochem., 56(2), 320-323 (1992) (Year: 1992).

Tanaka, J., et al., "Significance of Blood Ketone Body Ration as an indicator of Hepatic Cellular Energy Status in Jaundiced Rabbits", Gastroenterology, 1979, vol. 76, No. 4, pp. 691-696.

Tisdale, "Reduction of weight loss and tumour size in a cachexia model by a high fat diet", British Journal of Cancer, Jul. 1987, vol. 56, p. 39-43.

Vandenberghe et al. In Can. J. Physiol. Pharmacol. 95:455-458 (2017) (Published at www.nrcresearchpress.com/cjpp on Nov. 25, 2016). (Year: 2016).

Veech, et al., "Ketone Bodies Mimic the Life Span Extending Properties of Caloric Restriction", IUBMB Life Feb. 8, 2017.

Veech, Richard L. "The Therapeutic Implications of Ketone Bodies: The Effects of Ketone Bodies in Pathological Conditions: Ketosis, Ketogenic Diet, Redox States, Insulin Resistance, and Mitochondrial Metabolism." Prostaglandins Leukot Essent Fatty Acids. Mar. 2004;70(3):309-19.

Vorgerd, M. and J. Zange. Treatment of glycogenosys type V (McArdle disease) with creatine and ketogenic diet with clinical scores and with 31P-MRS on working leg muscle. Acta Myologica, 2007; XXVI; pp. 61-63.

Acetoacetate, Acetone, and Dibenzylamine (A Contaminant in L-(+)-Beta-Hydroxybutyrate) Exhibit Direct Anticonvulsant Actions In Vivo, Epilepsia, Raven Press Ltd, New York, US, vol. 43, No. 4, Apr. 1, 2002 (Apr. 1, 2002), pp. 358-361.

Haces M L et al: "Antioxidant capacity contributes to protection of ketone bodies against oxidative damage induced during hypoglycemic conditions", Experimental Neurology, Elsevier, Amsterdam, NL, vol. 211, No. 1, May 1, 2008 (May 1, 2008), pp. 85-96.

Stubbs et al., "On the Metabolism of Exogenous Ketones in Humans", frontiers in Physiology, vol. 8, 2017, 13 pages.

Tsai et al., "Stereoselective effects of 3-hydroxybutyrate on glucose utilization of rat cardiomyocytes" life Sciences 78(2006) pp. 1385-1391.

Cresci, G. et al., Lactobacillus GG and Tributyrin Supplementation Reduce Antibiotic-Induced Intestinal Injury, 2013, Journal of Parenteral and Enteral Nutrition, 37(6), 1-20 (Year: 2013).

Ichim, T. et al., Experimental support for the effects of a probiotic/digestive enzyme supplement on serum cholesterol concentrations and the intestinal microbiome, 2016, Journal of Translational Medicine, 14(184), 1-9 (Year: 2016).

Malo, M. S. et al., Intestinal alkaline phosphatase preserves the normal homeostasis of gut microbiota, 2010, Gut, 59, 1476-1484 (Year: 2010).

Blazquez et al. Journal of Neurochemistry, 1999, vol. 72 No. 4, pp. 1759-1768. (Year: 1999).

Craciun, S. et al. Microbial conversion of choline to trimethylamine requires a glycyl radical enzyme, 2012, PNAS, 109(52): 21307-21312 (Year: 2012).

International Preliminary Report on Patentability received for PCT Patent Application No. PCT/US2020/016952, dated Aug. 26, 2021, 7 pages.

International Preliminary Reporton Patentability received for PCT Patent Application No. PCT/US2020/017552, dated Aug. 26, 2021, 7 pages.

International Preliminary Reporton Patentability received for PCT Patent Application No. PCT/US2020/017555, dated Aug. 26, 2021, 7 pages.

International Preliminary Reporton Patentability received for PCT Patent Application No. PCT/US2020/017556, dated Aug. 26, 2021, 7 pages.

International Preliminary Reporton Patentability received for PCT Patent Application No. PCT/US2020/033159, dated Nov. 25, 2021, 6 pages.

International Search Report and Written Opinion received for PCT Patent Application No. PCT/US20/017555, dated May 4, 2020, 8 pages.

Amazon, "Perfect Keto Perform Pre Workout Powder—Burn Fat for Fuel Energy Supplement Drink Mix for Men and Women—Keto Friendly with Ketone Salts, BCAA, Nitric Oxide & MCT", Sep. 25, 2017 entire document especially p. 1 Retrieved from https://www.amazon.com/Perfect-Keto-Perform-PreworkoutSupplement/dp/B0751379Q9/ref=sr_1_9?dchild=1 &keywords=ketone+pre+workout &qid= 1597938465&sr=8-9.

Extended European Search Report received for EP Patent Application No. 19788264.0, dated Dec. 20, 2021, 11 pages.

International Preliminary Report on Patentability received for PCT Patent Application No. PCT/US20/37289, dated Dec. 30, 2021, 6 pages.

International Search Report and Written Opinion received for PCT Patent Application No. PCT/US21/045186, dated Nov. 22, 2021, 10 pages.

Kim Do Young et al., "Ketone bodies are protective against oxidative stress in neocortical neurons," Journal of Neurochemistry, vol. 101, Issue 5, Jun. 1, 2007, pp. 1316-1326.

Maalouf Met al., "Ketones inhibit mitochondrial production of reactive oxygen species production following glutamate excitotoxicity by increasing NADH oxidation," Neuroscience, New York, NY, US, vol. 145, Issue 1, Mar. 2, 2007, pp. 256-264.

(56) References Cited

OTHER PUBLICATIONS

Maalouf Met al., "The neuroprotective properties of calorie restriction, the ketogenic diet, and ketone bodies," Brain Research Reviews, Elsevier, NL, vol. 59, No. 2, Mar. 1, 2009, pp. 293-315.
Pete J Cox et al., "Acute nutritional ketosis: implications for exercise performance and metabolism," Extreme Physiology & Medicine, vol. 3, Issue 1, Dec. 1, 2014, pp. 1-9.

* cited by examiner

RACEMIC AND NEAR RACEMIC BETA-HYDROXYBUTYRATE MIXED SALT-ACID COMPOSITIONS

CROSS-REFERENCE TO RELATED APPLICATIONS

This application is a continuation-in-part of U.S. patent application Ser. No. 16/783,956, filed Feb. 6, 2020, which claims the benefit of U.S. Prov. App. No. 62/805,054, filed Feb. 13, 2019, which are incorporated by reference in their entirety.

BACKGROUND

1. Field of the Invention

Disclosed are racemic and near racemic beta-hydroxybutyrate compounds, particularly salts and acids of racemic or near racemic beta-hydroxybutyrate, and methods of administering racemic or near racemic beta-hydroxybutyrate mixed salt-acid compositions for producing elevated blood levels of ketone bodies in a subject.

2. Related Technology

In periods of fasting, extreme exercise, and/or low carbohydrate consumption, glucose and glycogen stores in the body are rapidly used and can become quickly depleted. Failure to replenish glucose stores as they become depleted causes the body to metabolically shift to the creation and use of ketone bodies for energy ("ketosis"). Ketone bodies can be used by cells of the body as a fuel to satisfy the body's energy needs, including the brain and heart. During prolonged fasting, for example, blood ketone levels can increase to 2-3 mmol/L or more. It is conventionally understood that when blood ketones rise above 0.5 mmol/L, the heart, brain and peripheral tissues are using ketone bodies (e.g., beta-hydroxybutyrate and acetoacetate) as the primary fuel source. This condition is referred to as ketosis. At blood levels between 1.0 mmol/L and 3.0 mmol/L the condition is called "nutritional ketosis."

Upon transitioning into ketosis, or in other words, during ketogenic metabolism in the liver, the body uses dietary and bodily fats as a primary energy source. Consequently, once in ketosis, one can induce loss of body fat by controlling dietary fat intake and maintaining low carbohydrate intake and blood level to sustain ketosis.

During ketosis, the body is in ketogenesis and essentially burning fat for its primary fuel. The body cleaves fats into fatty acids and glycerol and transforms fatty acids into acetyl CoA molecules, which are then eventually transformed through ketogenesis into the water-soluble ketone bodies beta-hydroxybutyrate (i.e., "β-hydroxybutyrate" or "BHB"), acetoacetate (also known as acetylacetonate), and acetone in the liver. Beta-hydroxybutyrate and acetoacetate are the primary ketone bodies used by the body for energy while acetone is removed and expelled as a by-product of ketogenesis.

The metabolism of ketone bodies is associated with several beneficial effects, including anticonvulsant effects, enhanced brain metabolism, neuroprotection, muscle sparing properties, and improved cognitive and physical performance. Science-based improvements in efficiency of cellular metabolism, managed through ketone supplementation, can have beneficial impacts on physical, cognitive health, and psychological health, and a long-term impact on health with respect to common avoidable diseases such as obesity, cardiovascular disease, neurodegenerative diseases, diabetes, and cancer.

Despite the many health advantages of pursuing a ketogenic diet or lifestyle and maintaining a state of nutritional ketosis, there remain significant barriers to pursuing and maintaining a ketogenic state. One of these barriers is the difficulty of transitioning into a ketogenic state. The fastest endogenous way to enter ketosis is by depleting glucose stores in the body through fasting combined with exercise. This is physically and emotionally demanding and is extremely challenging even for the most motivated and disciplined.

Additionally, the transition into ketosis is often accompanied by hypoglycemia, which can cause lethargy and light-headedness in many, resulting in an uncomfortable physiological and mental state commonly referred to as the "low-carb flu." In addition, many people experience a down regulation in their metabolism as the body naturally goes into an "energy-saving" mode. Some suggest that these transitory symptoms may last as long as two to three weeks. During this transition period, if a subject consumes a meal or snack containing carbohydrates above the restrictive amount, there is an immediate termination of ketogenesis, exiting the body from its state of ketosis. The body then shifts back to glucose utilization for its primary fuel and the transition into ketosis must begin anew.

If a subject is successful in establishing ketosis, the act of sustaining ketosis is likewise difficult, if not more difficult, due to the need to maintain a rigid dietary ratio of carbohydrates and protein to fats. It is further complicated by the disruption of normal electrolyte balances that often occurs when transitioning into and maintaining a ketogenic state. The depletion and lowering of glycogen stores in the liver and muscles lessens the ability of the body to retain water, leading to more frequent urination, and accordingly, a greater loss of electrolytes. Further, the reduction in insulin levels caused by ketosis effects the rate at which certain electrolytes are extracted by the kidneys, which can additionally lower electrolyte levels in the body. Negative effects of electrolyte imbalance include muscle aches, spasms, twitches and weakness, restlessness, anxiety, frequent headaches, feeling very thirsty, insomnia, fever, heart palpitations or irregular heartbeats, digestive issues such as cramps, constipation or diarrhea, confusion and trouble concentrating, bone disorders, joint pain, blood pressure changes, changes in appetite or body weight, fatigue (including chronic fatigue syndrome), numbness in joints, and dizziness, especially when standing up suddenly.

Some compositions used to promote ketosis in a mammal include those disclosed in U.S. Patent Publication No. 2017/0296501 to Lowery et al., which contain the endogenous form of beta-hydroxybutyrate, or R-beta-hydroxybutyrate, while Lowery et al. discourage use of the non-endogenous enantiomer, or S-beta-hydroxybutyrate, and racemic mixtures of R- and S-beta-hydroxybutyrate. Others, such as those disclosed in U.S. Pat. No. 8,642,654 to Clarke et al. consist mostly or entirely of a single beta-hydroxybutyrate ester (3R)-hydroxybutyl (3R)-hydroxybutyrate. The omission of enantiomers that are not the endogenous form of beta-hydroxybutyrate is based on the view that S-beta-hydroxybutyrate (aka (3S)-hydroxybutyrate) is ineffective or even harmful.

BRIEF SUMMARY

Disclosed herein are racemic and near racemic R- and S-beta-hydroxybutyrate mixed salt-acid compositions and methods of use in increasing ketone body level in a subject, including promoting and/or sustaining ketosis in a subject over an extended period of time.

The racemic and near racemic R- and S-beta-hydroxybutyrate mixed salt-acid compositions disclosed herein comprise a racemic or near racemic mixture of R-beta-hydroxybutyrate salt(s) and S-beta-hydroxybutyrate salt(s) ("R,S-beta-hydroxybutyrate salts") and a racemic or near racemic mixture of R-beta-hydroxybutyric acid and S-beta-hydroxybutyric acid ("R,S-beta-hydroxybutyric acids").

A "racemic mixture" of R,S-beta-hydroxybutyrate salts includes enantiomerically equivalent amounts (50:50) of R- and S-beta-hydroxybutyrate salts. A "racemic mixture" of R,S-hydroxybutyric acids includes enantiomerically equivalent amounts (50:50) of R- and S-beta-hydroxybutyric acids.

A "near racemic mixture" of R,S-beta-hydroxybutyrate salts includes non-equivalent amounts of R- and S-beta-hydroxybutyrate salts, such as from about 48%, 48.5%, 49%, 49.5%, or 49.8% to less than 50% by enantiomeric equivalents of one of R- or S-beta-hydroxybutyrate salt(s) and greater than 50% and up to about 52%, 51.5%, 51%, 50.5%, or 50.2% by enantiomeric equivalents of the other one of R- or S-beta-hydroxybutyrate salt(s).

A "near racemic mixture" of R,S-hydroxybutyric acids includes non-equivalent amounts of R- and S-beta-hydroxybutyric acids, such as from about 48%, 48.5%, 49%, 49.5%, or 49.8% to less than 50% by enantiomeric equivalents of one of R- or S-beta-hydroxybutyric acid and greater than 50% and up to about 52%, 51.5%, 51%, 50.5%, or 50.2% by enantiomeric equivalents of the other one of R- or S-beta-hydroxybutyric acid.

R-beta-hydroxybutyrate is the endogenous form produced by a mammal, and S-beta-hydroxybutyrate enters the body through exogenous supplementation through the administration of a racemic or near racemic RS-beta-hydroxybutyrate mixed salt-acid composition. The racemic or near racemic RS-beta-hydroxybutyrate mixed salt-acid compositions thus include separate components which function differently in the body but together provide enhanced ketogenic effects, including greater sustained blood ketone levels compared to the administration of only R-beta-hydroxybutyrate compounds. Racemic R,S-beta-hydroxybutyrate mixed salt-acid compositions provide at least a "double racemic stack" of beta-hydroxybutyrate compounds, while near racemic R,S-beta-hydroxybutyrate mixed salt-acid compositions provide a double stack comprising a slight excess of the R- or S-enantiomer and a sight deficiency of the other R- or S-enantiomer.

The R-beta-hydroxybutyrate enantiomer is endogenously produced by a mammal during ketosis, and the exogenously administered R-beta-hydroxybutyrate mixed salt-acid components thus provide an additional quantity and/or increased blood plasma level of R-beta-hydroxybutyrate that can be immediately utilized by the body, such as for producing energy (e.g., as an alternative energy source to glucose). The S-beta-hydroxybutyrate components, which are not endogenously produced by a mammal, complement the R-beta-hydroxybutyrate components, and produce one or more desired effects in the mammal not produced by the R-beta-hydroxybutyrate components.

For example, administering the S-beta-hydroxybutyrate mixed salt-acid components along with the R-beta-hydroxybutyrate mixed salt-acid components in enantiomerically equivalent or near enantiomerically equivalent ratios can result in at least one of: (1) increased endogenous production of R-beta-hydroxybutyrate and acetoacetate; (2) endogenous conversion of the S-beta-hydroxybutyrate components into one or both of R-beta-hydroxybutyrate and acetoacetate; (3) endogenous conversion of the S-beta-hydroxybutyrate components into fatty acids and sterols; (4) prolonged ketosis; (5) metabolism of the S-beta-hydroxybutyrate components independent of conversion to R-beta-hydroxybutyrate and/or acetoacetate; (6) increased fetal development; (7) increased growth years; (8) reduced endogenous production of acetone during ketosis; (9) signaling by the S-beta-hydroxybutyrate components that modulates metabolism of R-beta-hydroxybutyrate and glucose; (10) antioxidant activity; and (11) production of acetyl-CoA.

By way of further example, exogenous delivery of a racemic or near racemic R,S-beta-hydroxybutyrate mixed salt-acid composition can beneficially provide a relatively rapid boost to blood ketone body levels, primarily by way of the R-beta-hydroxybutyrate mixed salt-acid components, particularly R-beta hydroxybutyric acid, in addition to a relatively more sustained addition to blood ketone body level primarily by way of the S-beta-hydroxybutyrate mixed salt-acid components. Such racemic or near racemic R,S-beta-hydroxybutyrate mixed salt-acid compositions are thus capable of effectively and relatively rapidly aiding a subject in inducing ketosis, while simultaneously providing for sustained and prolonged delivery of ketone bodies to the blood stream by virtue of the modulating effects of the S-beta-hydroxybutyrate mixed salt-acid components in providing ketogenic benefits as required by the body.

Combining R- and S-beta-hydroxybutyric acid with one or more R- and S-beta-hydroxybutyrate salts is highly beneficial because it reduces electrolyte load, increases absorption rate, improves taste, facilitates easier formulation, and reduces the need to add citric acid or other edible acids to obtain a composition having neutral or acidic pH.

In some embodiments, the racemic or near racemic R,S-beta-hydroxybutyrate mixed salt-acid compositions described herein may be combined with (e.g., directly admixed with or co-administered with) one or more other dietetically and/or pharmaceutically acceptable supplements/drugs to form a combination supplement. The unique properties of a racemic or near racemic R,S-beta-hydroxybutyrate mixed salt-acid composition may beneficially enhance the combination supplement as compared to an otherwise similar combination supplement using a beta-hydroxybutyrate composition consisting of or highly enriched with either R-beta-hydroxybutyrate or S-beta-hydroxybutyrate. For example, a composition intended to increase lipolysis and/or fat oxidation (referred to herein as a "fat burner" component) may be combined with a racemic or near racemic R,S-beta-hydroxybutyrate mixed salt-acid composition to form a combination supplement with synergistic lipolysis and/or fat burning effects. In another example, a composition intended to increase enhance mental alertness, cognition, and/or mood (referred to herein as a "nootropic" component) may be combined with a racemic or near racemic R,S-beta-hydroxybutyrate mixed salt-acid composition to form a combination supplement with synergistic cognitive, alertness, and/or mood effects.

In some embodiments, the racemic or near racemic R,S-beta-hydroxybutyrate mixed salt-acid compositions disclosed herein can be used in a method for increasing ketone body level in a subject, including promoting and/or sustaining ketosis in a subject, comprising administering to a subject in need thereof a nutritionally or pharmaceutically effective amount of one or more compositions disclosed herein. Examples of beneficial effects of increased ketone body level in a subject include one or more of appetite suppression, weight loss, fat loss, reduced blood glucose level, improved mental alertness, anxiolytic effects (anti-anxiety), faster reaction time, increased physical energy, improved cognitive function, reduction in traumatic brain injury, reduction in effect of diabetes, improvement of neurological disorder, reduction of cancer, reduction of inflammation, anti-aging, antiglycation, reduction in epileptic seizure, improved mood, increased strength, increased muscle mass, or improved body composition.

In some embodiments, the composition may include a nutritionally or pharmaceutically acceptable carrier.

Embodiments include a "racemic stack" or "near racemic stack" of at least four different beta-hydroxybutyrate compounds. R-beta-hydroxybutyrate and S-beta-hydroxybutyrate are provided as free acids (i.e., R-beta-hydroxybutyric acid and S-beta-hydroxybutyric acid), salts thereof (i.e., R-beta-hydroxybutyrate salt(s) and S-beta-hydroxybutyrate salt(s)), and optionally esters thereof (i.e., R-beta-hydroxybutyrate ester(s) and S-beta-hydroxybutyrate ester(s)). Providing beta-hydroxybutyrate as a double racemic or near racemic stack that combines at least four separate forms (or triple racemic or near racemic stack that combines six separate forms) of beta-hydroxybutyrate may beneficially allow the use of higher amounts of beta-hydroxybutyrate for a given administered dose and/or allow for more doses per day. Each form of beta-hydroxybutyrate is typically associated with its own particular positive attributes and negative side effects. Stacking different forms of beta-hydroxybutyrate allows for delivery of more of the positive attributes compared to each being used alone. Similarly, stacking different forms of beta-hydroxybutyrate reduces or mitigates the negative side effects of each particular form of beta-hydroxybutyrate so that such negative effects can be "spread-out" and limited. In either case, stacking increases or maximizes the overall dose of beta-hydroxybutyrate that can be efficaciously delivered.

Additional features and advantages will be set forth in part in the description that follows, and in part will be obvious from the description, or may be learned by practice of the embodiments disclosed herein. It is to be understood that both the foregoing brief summary and the following detailed description are exemplary and explanatory only and are not restrictive of the embodiments disclosed herein or as claimed.

DETAILED DESCRIPTION

I. Definitions

Figure 1A:
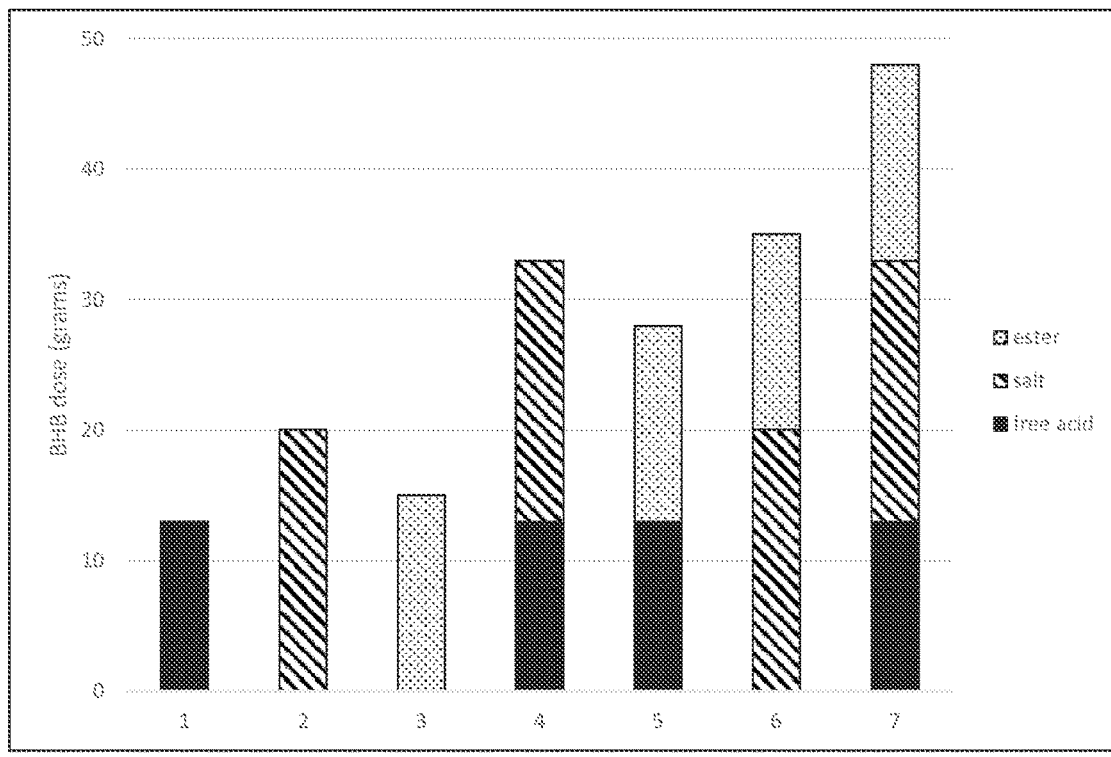
FIG. 1A illustrates higher levels of the amount of beta-hydroxybutyrate administered when using a "stacked" dose of at least two different forms of racemic or near racemic R,S-beta-hydroxybutyrate as compared to single forms of racemic or near racemic R,S-beta-hydroxybutyrate.

The compound "beta-hydroxybutyrate," also known as β-hydroxybutyrate, 3-hydroxybutyrate, βHB, or BHB, is the deprotonated form of beta-hydroxybutyric acid, which is a hydroxycarboxylic acid having the general formula $CH_3CH_2OHCH_2COOH$. The deprotonated form present at typical biological pH levels is $CH_3CH_2OHCH_2COO^-$. The general chemical structure shown below represents beta-hydroxybutyrate compounds that may be utilized in the disclosed compositions:

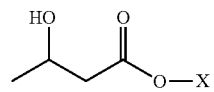

where,

X can be hydrogen, metal ion, amino cation such as from an amino acid, alkyl, alkenyl, aryl, or acyl.

When X is a hydrogen, the compound is beta-hydroxybutyric acid. When X is a metal ion or an amino cation, the compounds is a beta-hydroxybutyrate salt. When X is alkyl, alkenyl, aryl, or acyl, the compounds is a beta-hydroxybutyrate ester. The foregoing compounds can be in any desired physical form, such as crystalline, powder, solid, liquid, solution, suspension, or gel.

The term "racemic R,S-beta-hydroxybutyrate" means there are enantiomerically equivalent amounts (50:50) of total R- and S-beta-hydroxybutyrate compounds in the composition. The terms "racemic R,S-beta-hydroxybutyrate salt" and "racemic R,S-beta-hydroxybutyrate salts" mean there are enantiomerically equivalent amounts (50:50) of total R- and S-beta-hydroxybutyrate salts in the composition. The term "racemic R,S-beta-hydroxybutyric acid" means there are enantiomerically equivalent amounts (50:50) of total R- and S-beta-hydroxybutyric acids in the composition. The terms "racemic R,S-beta-hydroxybutyrate ester" and "racemic R,S-beta-hydroxybutyrate esters" mean there are enantiomerically equivalent amounts (50:50) of total R- and S-beta-hydroxybutyrate esters in the composition.

The term "near racemic R,S-beta-hydroxybutyrate" means there are non-equivalent amounts of total R- and S-beta-hydroxybutyrate compounds in the composition, such as from about 48%, 48.5%, 49%, 49.5%, or 49.8% to less than 50% by enantiomeric equivalents of one of R- or S-beta-hydroxybutyrate compounds and greater than 50% and up to about 52%, 51.5%, 51%, 50.5%, or 50.2% by enantiomeric equivalents of the other one of R- or S-beta-hydroxybutyrate compounds. The terms "near racemic R,S-beta-hydroxybutyrate salt" and "near racemic R,S-beta-hydroxybutyrate salts" mean there are non-equivalent amounts of total R- and S-beta-hydroxybutyrate salts in the composition, such as from about 48%, 48.5%, 49%, 49.5%, or 49.8% to less than 50% by enantiomeric equivalents of one of total R- and S-beta-hydroxybutyrate salt(s) and greater than 50% and up to about 52%, 51.5%, 51%, 50.5%, or 50.2% by enantiomeric equivalents of the other one of R- or S-beta-hydroxybutyrate salt(s). The term "near racemic R,S-beta-hydroxybutyric acid" means there are non-equivalent amounts of total R- and S-beta-hydroxybutyric acids in the composition, such as from about 48%, 48.5%, 49%, 49.5%, or 49.8% to less than 50% by enantiomeric equivalents of one of R- or S-beta-hydroxybutyric acid and greater than 50% and up to about 52%, 51.5%, 51%, 50.5%, or 50.2% by enantiomeric equivalents of the other one of R- or S-beta-hydroxybutyric acid. The terms "near racemic R,S-beta-hydroxybutyrate ester" and "near racemic R,S-beta-hydroxybutyrate esters" mean there are non-equivalent amounts of total R- and S-beta-hydroxybutyrate esters in the composition, such as from about 48%, 48.5%, 49%, 49.5%, or 49.8% to less than 50% by enantiomeric equivalents of one of total R- and S-beta-hydroxybutyrate ester(s) and greater than 50% and up to about 52%, 51.5%, 51%, 50.5%, or 50.2% by enantiomeric equivalents of the other one of R- or S-beta-hydroxybutyrate ester(s).

The term "R,S-beta-hydroxybutyrate mixed salt-acid composition" means there are enantiomerically equivalent or near equivalent amounts of one or more R-beta-hydroxybutyrate salts and one or more S-beta-hydroxybutyrate salts in the composition, and there are enantiomerically equivalent or near enantiomerically equivalent amounts of free R-beta-hydroxybutyric acid and free S-beta-hydroxybutyric acid in the composition.

The term "R,S-beta-hydroxybutyrate salt" does not mean or imply any particular physical state, such as a crystalline, powder, other solid form, dissolved in water to form a liquid solution, dispersed in a liquid to form a suspension, or gel. A salt can be formed in solution, such as by at least partially neutralizing beta-hydroxybutyric acid with a strong or weak base, such as an alkali or alkaline earth metal hydroxide, carbonate, or bicarbonate, basic amino acid, and the like.

The term "free beta-hydroxybutyric acid" means the sum of non-deprotonated and deprotonated beta-hydroxybutyric acid molecules. A deprotonated beta-hydroxybutyric acid molecule generally means a molecule that has released a proton to form a hydronium ion ($H_3O+$) and a beta-hydroxybutyrate anion (e.g., dissolved in water).

Free beta-hydroxybutyric acid molecules are typically not deprotonated to any significant degree when contained in a beta-hydroxybutyrate mixed salt-acid composition in dry powder or other solid form. In such cases, the fractional amount of free beta-hydroxybutyric acid in a beta-hydroxybutyrate mixed salt-acid composition on a weight basis is the weight of free beta-hydroxybutyric acid divided by the combined weight of free beta-hydroxybutyric acid and beta-hydroxybutyrate salt(s). On a molar basis, the fractional amount of free beta-hydroxybutyric acid in an beta-hydroxybutyrate mixed salt-acid composition are the molar equivalents of free beta-hydroxybutyric acid divided by the sum of molar equivalents of free beta-hydroxybutyric acid and beta-hydroxybutyrate anions provided by the beta-hydroxybutyrate salt(s).

When dissolved in water, a portion of the beta-hydroxybutyric acid will typically dissociate into beta-hydroxybutyrate anions and hydronium ions ($H_3O+$). As a result, beta-hydroxybutyric acid molecules can exchange protons and cations with dissolved beta-hydroxybutyrate salts. For purposes of defining the relative amounts of beta-hydroxybutyric acid and beta-hydroxybutyrate salt(s) in a beta-hydroxybutyrate mixed salt-acid composition, dissociation of beta-hydroxybutyric acid molecules and the exchange of protons and cations is not understood as changing the molar ratio of free beta-hydroxybutyric acid relative to beta-hydroxybutyrate anions from the beta-hydroxybutyrate salt(s). The total quantity of free beta-hydroxybutyric acid molecules in solution is the sum of dissolved beta-hydroxybutyric acid molecules that are not deprotonated and beta-hydroxybutyrate anions formed by deprotonation of beta-hydroxybutyric acid molecules.

Stated another way, the total molar equivalents of beta-hydroxybutyric acid in solution, whether or not deprotonated, is understood to be the difference between (i) the sum of molar equivalents of non-deprotonated beta-hydroxybutyric acid molecules and total molar equivalents of beta-hydroxybutyrate anions in solution (from all sources) and (ii) the total molar equivalents of cationic charge provided by cations from the beta-hydroxybutyrate salt compounds (which equals the total molar equivalents of beta-hydroxybutyrate anions provided by the beta-hydroxybutyrate salt(s)). Alkali metal cations such as sodium and potassium provide 1 mole of cationic charge per mole of metal cations. Alkaline earth metal cations such as magnesium and calcium, on the other hand, provide 2 moles of cationic charge per mole of metal cations. 1 mole of deprotonated beta-hydroxybutyric acid molecules provide 1 mole of anionic charge and one mole of cationic charge.

In view of the foregoing, the molar fraction of beta-hydroxybutyric acid in solution in relation to total moles of beta-hydroxybutyrate molecules from the beta-hydroxybutyrate mixed salt-acid composition in solution is [(i)−(ii)÷(i)], and the molar fraction of beta-hydroxybutyrate molecules from the beta-hydroxybutyrate salt(s)) in solution is [(ii)÷(i)]. Multiplying the molar fraction of each by 100 gives the percentage of each in solution.

By way of example, if 100 molar equivalents of beta-hydroxybutyrate mixed salt-acid composition in a dry powdered state contained 5% of free non-deprotonated beta-hydroxybutyric acid and 95% beta-hydroxybutyrate salt(s) on a molar basis, there would be essentially 5 molar equivalents of beta-hydroxybutyric acid molecules and 95 molar equivalents of beta-hydroxybutyrate anions. When there is sufficient water to dissolve the beta-hydroxybutyrate salt(s), and if a portion of the beta-hydroxybutyric acid molecules were deprotonated, the molar equivalents of non-deprotonated beta-hydroxybutyric acid would be less than 5, and the molar equivalents of beta-hydroxybutyrate anions would be greater than 95. The extent of deprotonation of beta-hydroxybutyric acid in solution is related to solution pH.

Whether beta-hydroxybutyrate is the R- or S-enantiomer depends on the tetrahedral orientation of the hydroxy on the 3-carbon (beta-carbon) in relationship to the planar carboxyl group.

Beta-hydroxybutyrate, typically R-beta-hydroxybutyrate, which is the endogenous form produced by mammals, can be utilized by a patient's body as a fuel source during instances of low glucose levels in the subject or when a patient's body is supplemented with a usable form of beta-hydroxybutyrate. Beta-hydroxybutyrate is commonly referred to as a "ketone body."

As used herein, a "ketogenic composition" is formulated to increase ketone body level in a subject, including inducing and/or sustaining a state of elevated ketone bodies at a desired level, such as ketosis, in a subject to which it is administered.

As used herein, "subject" or "patient" refers to members of the animal kingdom, including mammals, such as but not limited to, humans and other primates; rodents, fish, reptiles, and birds. The subject may be any animal requiring therapy, treatment, or prophylaxis, or any animal suspected of requiring therapy, treatment, or prophylaxis. Prophylaxis means that regiment is undertaken to prevent a possible occurrence, such as where a high glucose or diabetes is identified. "Patient" and "subject" are used interchangeably herein.

"Ketosis" as used herein refers to a subject having blood ketone levels, including both enantiomers of beta-hydroxybutyrate, acetoacetate and acetone, within the range of about 0.5 mmol/L and about 16 mmol/L in a subject. Ketosis may improve mitochondrial function, decrease reactive oxygen species production, reduce inflammation and increase the activity of neurotrophic factors. "Keto-adaptation" as used herein refers to prolonged nutritional ketosis (>1 week) to achieve a sustained nonpathological "mild ketosis" or "therapeutic ketosis."

In some cases, "elevated ketone body level" may not mean that a subject is in a state of "clinical ketosis" but nevertheless has an elevated supply of ketones for producing energy and/or for carrying out other beneficial effects of ketone body metabolism and signaling. For example, a subject that is "ketone adapted" may not necessarily have elevated blood serum levels of ketone bodies but rather is able to utilize available ketone bodies more rapidly compared to a subject that is not "ketone adapted." In such case, "elevated ketone body level" can refer to the total quantity and/or rate of ketone bodies being utilized by the subject rather than blood plasma levels per se.

The term "administration" or "administering" is used herein to describe the process in which the disclosed compositions are delivered to a subject. The composition may be administered in various ways including oral, intragastric, and parenteral (referring to intravenous and intra-arterial and other appropriate parenteral routes), among others.

The term "combination supplement" is used herein to describe the combination of beta-hydroxybutyrate compounds with one or more other supplements and/or drugs. The beta-hydroxybutyrate compounds and the one or more other supplements and/or drugs may be directly combined, such as by mixing together in the same tablet, capsule, mixed powder, or other dosage form, or such as by placing the separate components in the same packaging even if not directly mixed. In other embodiments, however, the separate components need not necessarily be directly combined prior to administration in order to fall within the scope of this disclosure. For example, the separate components may be administered to a subject separately but close enough in time (e.g., within about 8, 6, 4, 2, 1, or 0.5 hours of each other) to be considered co-administered and thus part of a "combination supplement."

II. Racemic and Near Racemic R,S-Beta-Hydroxybutyrate Mixed Salt-Acid Compositions In one aspect, compositions for increasing ketone body level in a subject, including promoting and/or sustaining ketosis, comprise racemic R,S-beta-hydroxybutyrate mixed salt-acid compositions, including (1) 50% by enantiomeric equivalents of one or more R-beta-hydroxybutyrate salts and 50% by enantiomeric equivalents of one or more S-beta-hydroxybutyrate salts and (2) 50% by enantiomeric equivalents of R-beta-hydroxybutyric acid and 50% by enantiomeric equivalents of S-beta-hydroxybutyric acid. The composition may optionally include 50% by enantiomeric equivalents of one or more R-beta-hydroxybutyrate esters and 50% by enantiomeric equivalents of one or more S-beta-hydroxybutyrate esters.

In another aspect, compositions for increasing ketone body level in a subject, including promoting and/or sustaining ketosis, comprise near racemic R,S-beta-hydroxybutyrate mixed salt-acid compositions, including (1) from about 48%, 48.5%, 49%, 49.5%, or 49.8% to less than 50% by enantiomeric equivalents of one or more salts of one of R- or S-beta-hydroxybutyrate and greater than 50% and up to about 52%, 51.5%, 51%, 50.5%, or 50.2% by enantiomeric equivalents of one or more salts of the other one of R- or S-beta-hydroxybutyrate and (2) from about 48%, 48.5%, 49%, 49.5%, or 49.8% to less than 50% by enantiomeric equivalents of one or R- or S-beta-hydroxybutyric acid and greater than 50% and up to about 52%, 51.5%, 51%, 50.5%, or 50.2% by enantiomeric equivalents of the other one of R- or S-beta-hydroxybutyric acid. The near racemic composition may optionally include from about 48%, 48.5%, 49%, 49.5%, or 49.8% to less than 50% by enantiomeric equivalents of one or more esters of one of R- or S-beta-hydroxybutyrate and greater than 50% and up to about 52%, 51.5%, 51%, 50.5%, or 50.2% by enantiomeric equivalents of one or more esters of the other one of R- or S-beta-hydroxybutyrate.

Racemic and near racemic mixtures of R,S-beta-hydroxybutyrate mixed salt-acid components can provide synergistic effects, such when used in combination with other components. In such case, the combined salt and acid forms of R,S-beta-hydroxybutyrate have acceptable pH and taste. Racemic and near racemic R,S-beta-hydroxybutyrate mixed salt-acid compositions have substantial advantages over R,S-beta-hydroxybutyrate salts and esters, including increased absorption rate, increased bioavailability, lower electrolyte load, ease of manufacture, significantly improved taste, and reduced need for citric acid or other edible acids to obtain a composition with neutral or acidic pH.

In some embodiments, the racemic or near racemic R,S-beta-hydroxybutyrate mixed salt-acid composition contains less than 100% of racemic or near racemic R,S-beta-hydroxybutyrate salts and greater than 0% of free racemic or near racemic R,S-beta-hydroxybutyric acids. Racemic or near racemic R,S-beta-hydroxybutyrate mixed salt-acid compositions may contain, on a molar basis, up to 99.9%, 99.8%, 99.7%, 99.6%, 99.5%, 99.4%, 99.3%, 99.2%, 99.1%, 99%, 98.8%, 98.65%, 98.5%, 98.35%, 98.2%, 98%, 97.75%, 97.5%, 97.25%, or 97%, and at least 75%, 80%, 85%, 90%, 92%, 94%, 95%, 96%, or 97%, of total racemic or near racemic R,S-beta-hydroxybutyrate salts and at least 0.1%, 0.2%, 0.3%, 0.4%, 0.5%, 0.6%, 0.7%, 0.8%, 0.9%, 1%, 1.2%, 1.35%, 1.5%, 1.65%, 1.8%, 2%, 2.25%, 2.5%, 2.75%, or 3%, and less than 25%, 20%, 15%, 10%, 8%, 6%, 5%, 4%, or 3%, of total free racemic or near racemic R,S-beta-hydroxybutyric acids. The foregoing percentages are expressed on a molar basis (e.g., moles of free R,S-beta-hydroxybutyric acids relative to total moles of R,S-beta-hydroxybutyrate compounds in both salt and acid forms).

The racemic or near racemic mixture of R-beta-hydroxybutyrate mixed salt-acid components and S-beta-hydroxybutyrate mixed salt-acid components contains equivalent or near equivalent amounts of the R-beta-hydroxybutyrate enantiomer, the endogenous form produced by a mammal, and the S-beta-hydroxybutyrate enantiomer, which is not produced or found naturally in mammals, in order to provide enhanced ketogenic effects not possible with either of the enantiomers delivered alone or in enriched form.

For example, the R-beta-hydroxybutyrate enantiomer is endogenously produced by a mammal during ketosis, and thus administering the R-beta-hydroxybutyrate mixed salt-acid components to a subject provides an additional quantity and/or increased blood plasma level that can be relatively immediately utilized by the body, such as for producing energy (e.g., as an alternative energy source to glucose). The presence of the S-beta-hydroxybutyrate mixed salt-acid components can modulate this effect in order to provide, for example, a more controlled, gradual, and/or extended ketogenic effect compared to a composition enriched with the R-beta-hydroxybutyrate mixed salt-acid components.

By way of further example, a racemic or near racemic R,S-beta-hydroxybutyrate mixed salt-acid composition can beneficially provide a relatively rapid boost to blood ketone body levels, primarily by way of the R-beta-hydroxybutyrate enantiomer components, in addition to a relatively more extended, sustained increase to blood ketone body levels primarily by way of the S-beta-hydroxybutyrate enantiomer components. Such compositions are thus capable of effectively and relatively rapidly aiding a subject in inducing ketosis, while simultaneously providing for sustained and prolonged delivery of ketone bodies to the blood stream, wherein the R-beta-hydroxybutyrate and S-beta-hydroxybutyrate components together provide synergistic ketogenic benefits to a subject.

Contrary to compositions that deliberately minimize or eliminate S-beta-hydroxybutyrate, the racemic or near racemic R,S-beta-hydroxybutyrate mixed salt-acid composition contains an equivalent or near equivalent quantity of the S-beta-hydroxybutyrate enantiomer, which is not endogenously produced by a mammal, in order to produce one or more desired effects in the mammal. For example, administering S-beta-hydroxybutyrate mixed salt-acid components along with R-beta-hydroxybutyrate mixed salt-acid components can result in at least one of: (1) increased endogenous production of R-beta-hydroxybutyrate and acetoacetate; (2) endogenous conversion of the S-beta-hydroxybutyrate components into one or both of R-beta-hydroxybutyrate and acetoacetate; (3) endogenous conversion of the S-beta-hydroxybutyrate components into fatty acids and sterols; (4) prolonged ketosis; (5) metabolism of the S-beta-hydroxybutyrate components independent of conversion to R-beta-hydroxybutyrate and/or acetoacetate; (6) increased fetal development; (7) increased growth years; (8) reduced endogenous production of acetone during ketosis; (9) signaling by the S-beta-hydroxybutyrate that modulates metabolism of R-beta-hydroxybutyrate and glucose; (10) antioxidant activity; and (11) production of acetyl-CoA.

The racemic or near racemic R,S-beta-hydroxybutyrate mixed salt-acid compositions can be used, for example, to produce one or more desired effects in the subject, including but not limited to, appetite suppression, weight loss, fat loss, reduced blood glucose level, improved mental alertness, increased physical energy, improved cognitive function, reduction in traumatic brain injury, reduction in effect of diabetes, improvement of neurological disorder, reduction of cancer, reduction of inflammation, anti-aging, antiglycation, reduction in epileptic seizure, improved mood, increased strength, increased muscle mass, or improved body composition.

In some embodiments, the racemic or near racemic R,S-beta-hydroxybutyrate mixed salt-acid compositions may include or be combined with a carrier, such as a dietetically or pharmaceutically acceptable carrier. Examples carrier or forms of the composition include powders, liquids, tablets, capsules, food products, food additives, beverages, vitamin fortified beverages, beverage additives, candies, suckers, pastilles, food supplements, sprays, injectables, and suppositories.

Examples of R,S-beta-hydroxybutyrate salts include one or more salts of alkali metals, alkaline earth metals, transition metals, amino acids, or metabolites of amino acids. Examples include lithium salts, sodium salts, potassium salts, magnesium salts, calcium salts, zinc salts, iron salts (as iron II and/or iron III), chromium salts, manganese salts, cobalt salts, copper salts, molybdenum salts, selenium salts, arginine salts, lysine salts, leucine salts, isoleucine salts, histidine salts, ornithine salts, citrulline salts, glutamine salts, and creatine salts.

In some embodiments, racemic or near racemic R,S-beta-hydroxybutyrate mixed salt-acid compositions may further include racemic or near racemic R,S-beta-hydroxybutyrate esters, such as mono-, di-, tri-, oligo-, and polyesters. Examples include mono-ester of ethanol, mono-ester of 1-propanol, mono-ester of 1,2-propanediol, di-ester of 1,2-propanediol, mono-ester of 1,3-propanediol, di-ester of 1,3-propanediol, mono-ester of S-, R-, or S-R-1,3-butanediol, di-ester of S-, R-, or S—R-1,3-butanediol, mono-ester of glycerin, (3 S)-hydroxybutyl (3 S)-hydroxybutyrate mono-ester, (3R)-hydroxybutyl (3 S)-hydroxybutyrate, mono-ester, di-ester of glycerin, tri-ester of glycerin, ester of acetoacetate, dimers, trimers, oligomers, and polyesters containing repeating units of beta-hydroxybutyrate, and complex oligomers or polymers of beta-hydroxybutyrate and one or more other hydroxy-carboxylic acids, such as lactic acid, citric acid, acetoacetic acid, quinic acid, shikimic acid, salicylic acid, tartaric acid, and malic acid, and/or beta-hydroxybutyrate and or one or more diols, such as 1,3-propanediol and 1,3-butanediol, one or more polyacids, such as tartaric acid, citric acid, malic acid, succinic acid, and fumaric acid, and short chain fatty acids, such as butyric acid, valeric acid, or caproic acid.

In some embodiments, the composition may further include or be combined with at least one short chain fatty acid, or a mono-, di- or triglyceride of the at least one short chain fatty acid, wherein the short chain fatty acid has less than 6 carbons. Example short chain fatty acids include acetic acid, propionic acid, butyric acid, isobutyric acid, valeric acid, and isovaleric acid. An example short chain triglyceride is tributyrin. Such molecules can provide protection to the gut and improve microbiome health.

The composition may include or be combined with at least one medium chain fatty acid, or a mono-, di- or triglyceride of the at least one medium chain fatty acid, wherein the medium chain fatty acid has from 6 to 12 carbons, preferably from 8 to 10 carbons. Example medium chain fatty acids are caproic acid, caprylic acid, capric acid, and lauric acid. Medium chain triglycerides (MCT), medium chain fatty acids, and mono- and di-glycerides are ketone body precursors that can provide an additional source for the production of ketone bodies independent of R-beta-hydroxybutyrate.

The composition may include or be combined with at least one long chain fatty acid, or a mono-, di- or triglyceride of the at least one long chain fatty acid, having more than 12 carbons. Examples of long-chain fatty acids include myristic acid, palmitic acid, stearic acid, arachidic acid, behenic acid, lignoceric acid, cerotic acid, omega-3 fatty acids, omega-6 fatty acids, omega-7 fatty acids, and omega-9 fatty acids.

Examples and sources of the medium chain fatty acid, or an ester thereof such as a medium chain triglyceride, include coconut oil, coconut milk powder, fractionated coconut oil, palm oil, palm kernel oil, caprylic acid, capric acid, isolated medium chain fatty acids, such as isolated hexanoic acid, isolated octanoic acid, isolated decanoic acid, medium chain triglycerides either purified or in natural form such as coconut oil, and ester derivatives of the medium chain fatty acids ethoxylated triglyceride, enone triglyceride derivatives, aldehyde triglyceride derivatives, monoglyceride derivatives, diglyceride derivatives, and triglyceride derivatives, and salts of the medium chain triglycerides. Ester derivatives optionally include alkyl ester derivatives, such as methyl, ethyl, propyl, butyl, hexyl, etc.

The administration of a racemic or near racemic mixture of R-beta-hydroxybutyrate mixed salt-acid components and S-beta-hydroxybutyrate mixed salt-acid components results in a dual effect providing both: (1) an initial and relatively immediate elevated blood level of ketone bodies; and (2) a later and relatively extended elevated blood level of ketone bodies, thereby exploiting the metabolic and physiological advantages of (1) quickly induced and (2) temporally sustained ketosis.

Raising the levels of ketone bodies in the blood through exogenous supplementation provides a subject with greater flexibility in diet options as compared to methods that aim to induce and sustain ketosis based on diet alone (e.g., based on fasting and/or limited carbohydrate intake). For example, a subject that has been administered an appropriate amount of a racemic or near racemic mixture of R-beta-hydroxybutyrate mixed salt-acid components and S-beta-hydroxybutyrate mixed salt-acid components will be able to eat an occasional carbohydrate or sugar-based food without jeopardizing the ketogenic state and shifting back into a glucose-based metabolic state. Further, such administration facilitates easier transitioning into a ketogenic state while reducing or eliminating the detrimental effects typically associated with entering ketosis.

In some embodiments, a ketogenic composition additionally includes a therapeutically effective amount of one or more vitamins and/or minerals. One example is vitamin $D_3$, which is believed to work in conjunction with magnesium and calcium to promote good bone health and to prevent undesirable calcification of soft tissues. In preferred embodiments, vitamin $D_3$ is included in an amount such that an average daily dose of the ketogenic composition includes about 200 IU ("International Units") to about 8000 IU, or about 400 IU to about 4000 IU, or about 600 IU to about 3000 IU of vitamin $D_3$. In some embodiments, vitamin $D_3$ is included in an amount such that an average daily dose of the ketogenic composition includes about 5 μg to about 200 μg, or about 10 μg to about 100 μg, or about 15 to about 75 μg of vitamin $D_3$.

Some embodiments also include one or more additional ketone precursors or supplements. These additional ketone precursors or supplements might include acetoacetate, ketone esters, and/or other compounds that cause a rise in blood ketone levels without adding more electrolytes to the bloodstream. Acetoacetate can be provided in salt form, ester form, acid form, and combinations thereof. Other additives include metabolites that enhance the effect or transport of ketone bodies into mitochondria, caffeine, theobromine, and nootropics, such as L-alpha glycerylphosphorylcholine ("alpha GPC").

The composition may include flavoring agents that help mask the occasionally poor taste of beta-hydroxybutyrate compounds (particularly when provided in a non-salt form). These include essential oils, such as peppermint, natural and artificial sweeteners, and other flavorants known in the art.

In some embodiments, ketogenic compositions may further include one or more additional components configured to lower the hygroscopicity of the composition. For example, various anticaking agents, flow agents, and/or moisture absorbers, in types and amounts that are safe for consumption, may be included. Such additional components may include one or more of an aluminosilicate, ferrocyanide, carbonate or bicarbonate salt, silicate (e.g., sodium or calcium silicate), silica, phosphate salt (e.g., di- or tricalcium phosphate), talc, powdered cellulose, calcium carbonate, and the like.

III. Stacking of Racemic or Near Racemic R,S-Beta-Hydroxybutyrate Compounds

As described above, the racemic or near racemic R,S-beta-hydroxybutyrate mixed salt-acid compositions described herein may be provided in three general forms: (1) racemic or near racemic R,S-beta-hydroxybutyrate salt(s), (2) racemic or near racemic R,S-beta-hydroxybutyric acid, and optionally (3) racemic or near racemic R,S-beta-hydroxybutyrate ester(s). The compositions described herein may be provided in "stacked" mixtures combining at least salt and acid forms and optionally ester forms Each of the different forms has its own properties and its own potential benefits and limitations. For example, ester forms of beta-hydroxybutyrate typically have poor organoleptic properties relative to the other forms of beta-hydroxybutyrate. That is, ester forms of beta-hydroxybutyrate are often described as having a pungent taste and/or smell.

Salt forms of R,S-beta-hydroxybutyrate are generally considered to taste better than ester forms. However, administration of clinically or dietetically effective doses of R,S-beta-hydroxybutyrate in salt form inherently requires administration of relatively high levels of the corresponding cations. Sodium, for example, is often used as the cation in beta-hydroxybutyrate salts, and high levels of sodium have well-known negative health effects. Although different beta-hydroxybutyrate salts having different cations may be mixed to dilute the impact of a single cation, it can still be difficult to provide effective amounts of beta-hydroxybutyrate without upsetting the electrolyte balance in the subject/patient.

The free acid form of racemic or near racemic R,S-beta-hydroxybutyrate (i.e., racemic or near racemic R,S-beta-hydroxybutyric acid) is therefore utilized to form the mixed salt-acid compositions. Because beta-hydroxybutyric acid has a pKa of 4.70, it deprotonates and produces $H^+$ at physiological pH. The resulting excess acidity can cause undesirable side effects including causing or aggravating gastrointestinal issues such as ulcers or reflux.

Combining different forms of racemic or near racemic R,S-beta-hydroxybutyrate is selected amounts can beneficially limit the occurrence and/or severity of these undesirable side-effects and/or can permit administration of higher doses of beta-hydroxybutyrate compounds. For example, a beta-hydroxybutyrate stack can deliver the same amount of beta-hydroxybutyrate as a single form without causing the same occurrence and/or severity of side-effects. Likewise, a combined form can deliver a greater amount of beta-hydroxybutyrate than a single form before reaching similar occurrence and/or severity of side-effects.

Figure 1B:
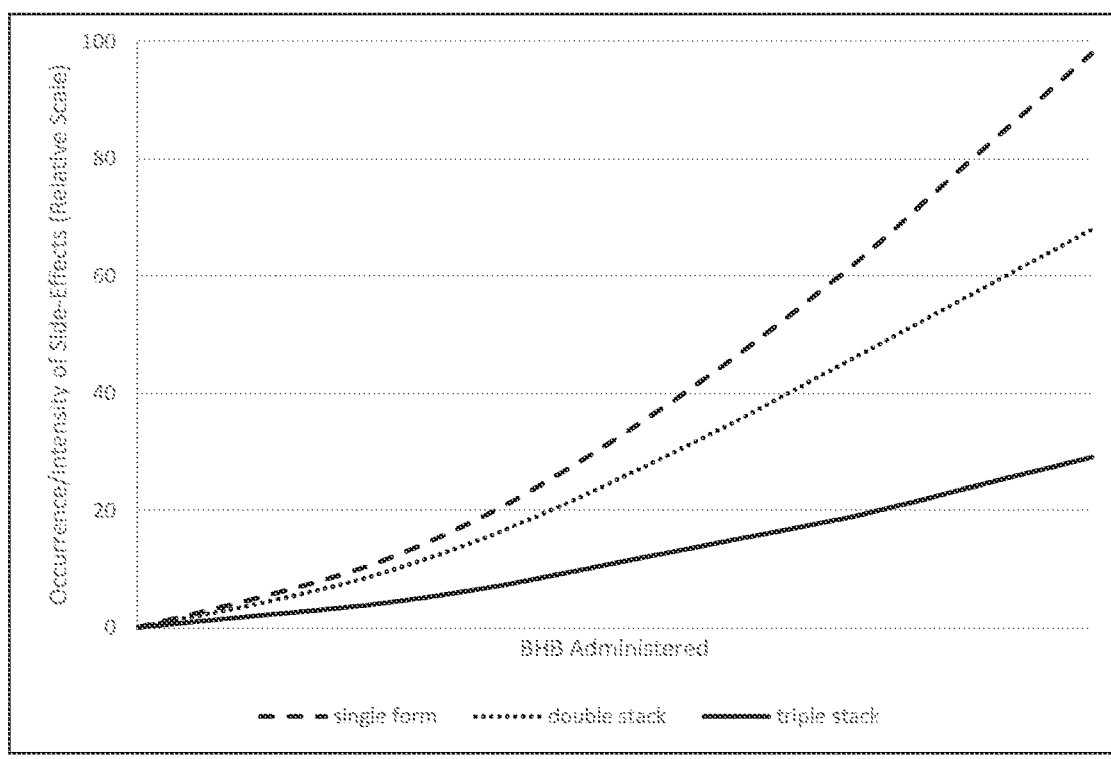
FIG. 1B illustrates expected relative rates of undesirable side-effects resulting from treatment with various formulations of beta-hydroxybutyrate, where a "double stack" (i.e., double racemic or near racemic stack) formulation comprising 1) free R,S-beta-hydroxybutyric acids and (2) R,S-beta-hydroxybutyrate salts and a "triple stack" (i.e., triple racemic or near racemic stack) formulation further comprising R,S-beta-hydroxybutyric esters on top of the double stack are expected to allow for administration of greater amounts of beta-hydroxybutyrate and/or reduced occurrences or intensities of side-effects as compared to administering single forms of beta-hydroxybutyrate.

This is schematically illustrated in FIGS. 1A and 1B. FIG. 1A shows different beta-hydroxybutyrate doses when using a single form (formulations 1-3), a double stack (formulations 4-6), and a triple stack (formulation 7). Although individual tolerances may vary and the illustrated doses are therefore exemplary only, a typical subject will want to avoid excessive amounts of any single form of beta-hydroxybutyrate in order to avoid the corresponding side effects. Accordingly, stacking different forms of beta-hydroxybutyrate allows for greater delivery of beta-hydroxybutyrate in a dose and/or allows for a higher dosing frequency as compared to use of the single form. For example, different forms of beta-hydroxybutyrate may be stacked in a single dose to allow for greater amounts of beta-hydroxybutyrate in the dose, and/or different forms of beta-hydroxybutyrate may be taken in different doses throughout the day to allow for greater dosing frequency and thus higher overall daily delivery of beta-hydroxybutyrate.

FIG. 1B shows expected relative severity of undesirable side-effects resulting from treatment with various formulations of beta-hydroxybutyrate, including stacked formulations. The triple stack formulation comprising each of 1) the salt form of beta-hydroxybutyrate, 2) the free acid form of beta-hydroxybutyrate (i.e., beta-hydroxybutyric acid), and 3) the ester form of beta-hydroxybutyrate is expected to allow for administration of a greater amount of beta-hydroxybutyrate and/or to have reduced side-effects as compared to a double stack comprising only two such forms of beta-hydroxybutyrate. Both the triple stack (i.e., triple racemic stack) and the double stack (i.e., double racemic stack) are likewise expected to allow for administration of a greater amount of beta-hydroxybutyrate and/or to have reduced side-effects as compared to a single form comprising only one form of beta-hydroxybutyrate.

In other words, for a given dose of beta-hydroxybutyrate, double and triple racemic stacks can be formulated to cause less 1) organoleptic side-effects, 2) electrolyte imbalance side-effects, and/or 3) acidity side-effects as compared to the single form. For example, a single form beta-hydroxybutyrate ester may have a threshold dosage that the typical user will not exceed because of the negative organoleptic side-effects, a single form beta-hydroxybutyrate salt may have a threshold dosage limited by the recommended dietary limits of the electrolytes administered with the salt, and a single form beta-hydroxybutyric acid may have a threshold dosage that the typical user will not exceed because of the negative effects of acidity. The stacked forms of beta-hydroxybutyrate allow for supplementation of greater amounts of beta-hydroxybutyrate without passing any of the separate thresholds related to organoleptic, electrolyte, or acidity side-effects.

In some embodiments, a beta-hydroxybutyrate stack includes at least two of: (i) one or more racemic or near racemic R,S-beta-hydroxybutyrate salts; (ii) racemic or near racemic R,S-beta-hydroxybutyric acid; and (iii) one or more beta-hydroxybutyrate esters. For example, a beta-hydroxybutyrate double stack may include at least two of components (i), (ii), and (iii) each provided at about 2% to about 98%, or about 5% to about 95%, or about, 10% to about 90%, or about 20% to about 80%, or about 30% to about 70%, or about 40% to about 60% on a molar basis of beta-hydroxybutyrate.

In some embodiments, a beta-hydroxybutyrate triple stack includes a beta-hydroxybutyrate ester at about 2% to about 96%, or about 5% to about 90%, or about 10% to about 80%, or about 20% to about 60% on a molar basis of beta-hydroxybutyrate, includes a beta-hydroxybutyrate salt at about 2% to about 96%, or about 5% to about 90%, or about 10% to about 80%, or about 20% to about 60% on a molar basis of beta-hydroxybutyrate, and includes beta-hydroxybutyric acid at about 2% to about 96%, or about 5% to about 90%, or about 10% to about 80%, or about 20% to about 60% on a molar basis of beta-hydroxybutyrate. In some embodiments, a beta-hydroxybutyrate triple stack includes each of the three forms of beta-hydroxybutyrate in substantially equal amounts on a molar basis of beta-hydroxybutyrate.

A stacked beta-hydroxybutyrate composition may also provide a more beneficial digestive release profile. Each of the different forms of beta-hydroxybutyrate may interact somewhat differently upon ingestion. For example, the free acid form may be readily delivered to the bloodstream as a usable ketone body, beta-hydroxybutyrate from salt forms may in general take slightly longer to reach the bloodstream depending on the solubility characteristics of the particular salt or salt mixture utilized, and beta-hydroxybutyrate from ester forms may in general take the longest to reach the bloodstream depending on how rapidly the ester bond undergoes hydrolysis. Thus, a stacked beta-hydroxybutyrate formulation can be tailored to provide a more preferable release profile, such as one that combines the benefits of more rapid onset with the benefits of a more extended release, and/or one that provides an overall greater pharmacokinetic area under the curve (AUC). Stacked compositions can provide for timed delivery or availability of ketone bodies, which provides for more even blood concentration of ketone bodies and a significantly longer delivery "tail" of exogenous ketone bodies, such as 1-8 hours after consuming the stacked composition.

Figure 2:
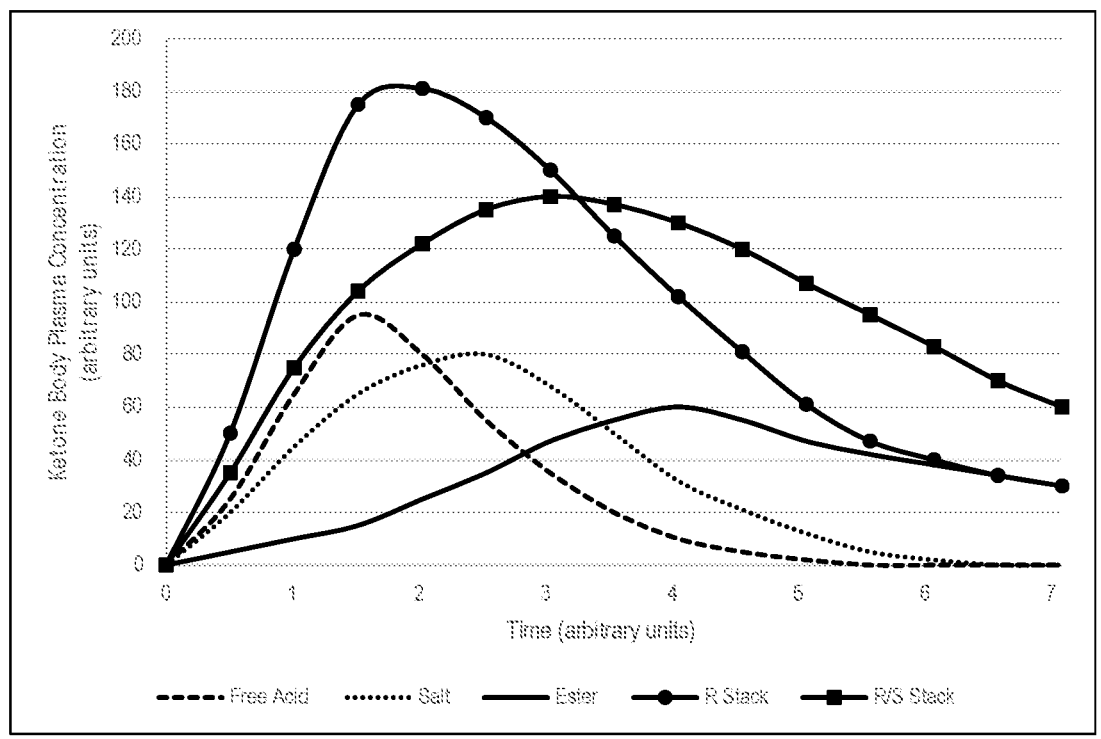
FIG. 2 compares expected release profiles of R,S-beta-hydroxybutyrate stack compositions to free acid, salt, and ester single forms and also an R-beta-hydroxybutyrate stack, illustrating that stacked R,S-compositions provide an overall release profile that is extended and has a larger area under the curve (AUC)

This is illustrated in FIG. 2, which compares expected release profiles of keto stack compositions (e.g., comprising the free acid and salt) to each of the free acid, salt, and ester single forms. Because the keto stack compositions are able to provide more overall exogenous ketone bodies, and because they are provided in a plurality of different forms with different release characteristics, the overall release profile is extended and provides a larger AUC.

FIG. 2 also illustrates how a release profile may be adjusted by utilizing different relative amounts of S-beta-hydroxybutyrate and R-beta-hydroxybutyrate. As illustrated, the beta-hydroxybutyrate in the "R Stack" is comprised of R-beta-hydroxybutyrate, while the "R/S Stack" contains a racemic mixture of R-beta-hydroxybutyrate and S-beta-hydroxybutyrate, which flattens and extends the release profile.

IV. Combination Supplements

The ketogenic compositions described herein may be beneficially combined with one or more other dietetically and/or pharmaceutically acceptable supplements/drugs to form a combination supplement. The unique properties of a racemic or near racemic R,S-beta-hydroxybutyrate mixed salt-acid composition may beneficially enhance the combination supplement as compared to an otherwise similar combination supplement using a beta-hydroxybutyrate composition enriched more heavily in either R-beta-hydroxybutyrate or S-beta-hydroxybutyrate.

For example, a composition intended to increase lipolysis and/or fat oxidation (referred to herein as a "fat burner" component) may be combined with a racemic or near racemic R,S-beta-hydroxybutyrate component to form a combination supplement with synergistic lipolysis and/or fat burning effects. Without being bound to any particular theory, it is believed that the fat burner composition is more readily utilized when combined with a racemic or near racemic R,S-beta-hydroxybutyrate component as compared to when utilized without a beta-hydroxybutyrate component.

That is, the racemic or near racemic R,S-beta-hydroxybutyrate component may function to effectively "prime" the subject for more metabolically efficient utilization of lipids. as an energy source. For example, with exogenous supplementation of a racemic or near racemic R,S-beta-hydroxybutyrate mixed salt-acid composition, a subject is likely to ramp up the enzymes and other metabolic machinery necessary to utilize such ketone bodies (and thus stored body fat) as an energy source. The fat burner may therefore have enhanced pharmacokinetics and/or pharmacodynamics when co-administered, and thus may increase lipolysis and/or fat oxidation to levels higher than if either the beta-hydroxybutyrate component or the fat burner were administered in isolation.

Figure 3:
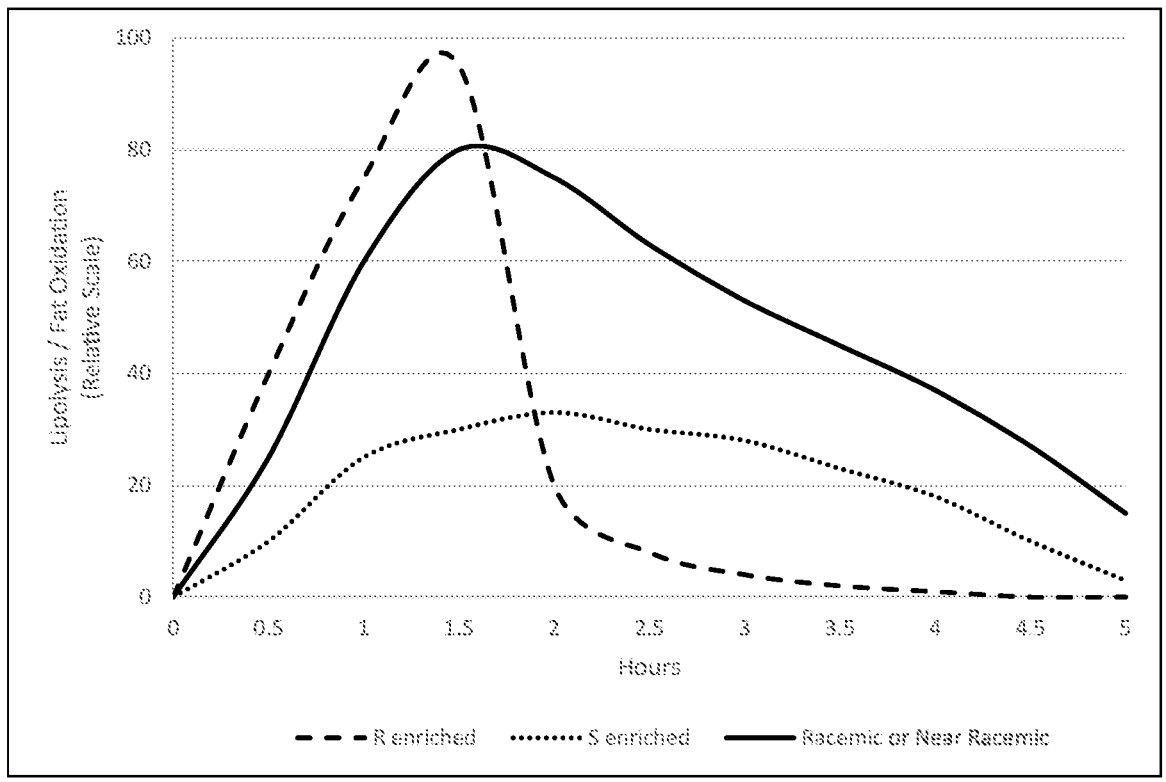
FIG. 3 illustrates expected relative rates of lipolysis and/or fat oxidation resulting from treatment with a combination weight loss supplement including a beta-hydroxybutyrate component in combination with another weight loss supplement, and showing total amount of lipolysis and/or fat oxidation (area under the curve) is higher for a combination supplement using racemic or near racemic R,S-beta-hydroxybutyrate components as compared to otherwise similar combination supplements/drugs using beta-hydroxybutyrate components consisting of or highly enriched with R-beta-hydroxybutyrate or S-beta-hydroxybutyrate.

These synergistic effects of a combination supplement are believed to be more pronounced when the beta-hydroxybutyrate component is a racemic or near racemic R,S-beta-hydroxybutyrate component as opposed to being enriched with either R-beta-hydroxybutyrate or S-beta-hydroxybutyrate. This is schematically illustrated in FIG. 3. As shown, for a combination supplement with a given beta-hydroxybutyrate dose, where the beta-hydroxybutyrate component is more highly enriched in R-beta-hydroxybutyrate, the level of fat oxidation/lipolysis is initially relatively high, but then tapers relatively rapidly. Where the beta-hydroxybutyrate component is more highly enriched in S-beta-hydroxybutyrate, the level of fat oxidation/lipolysis is more extended in duration than the enriched R-beta-hydroxybutyrate composition, but overall levels of fat oxidation/lipolysis remain relatively low throughout.

On the other hand, where the beta-hydroxybutyrate component is racemic or near racemic, the R-beta-hydroxybutyrate components and S-beta-hydroxybutyrate components function to provide a relatively high initial level of fat oxidation/lipolysis as well as a relatively extended duration of fat oxidation/lipolysis. Though perhaps the racemic or near racemic R,S-beta-hydroxybutyrate version does not provide an initial level of fat oxidation/lipolysis as high as with a more highly enriched R-beta-hydroxybutyrate version, and perhaps does not provide a duration of fat oxidation/lipolysis as long as with a more highly enriched S-beta-hydroxybutyrate version, the combined effects of the R-beta-hydroxybutyrate components and S-beta-hydroxybutyrate components, when provided in enantiomerically equivalent or near equivalent proportions, provide higher overall levels of fat oxidation/lipolysis. In other words, the area under the curve is greater where the racemic or near racemic R,S-beta-hydroxybutyrate composition is utilized in the combination supplement as compared to the more highly enriched R-beta-hydroxybutyrate or the more highly enriched S-beta-hydroxybutyrate.

The fat burner component may include one or more compounds capable of promoting enhanced lipolysis and/or fat oxidation. For example, the fat burner component may include green tea, green tea extract (e.g., a composition including one or more isolated green tea catechins such as epigallocatechin gallate (EGCG)), green coffee extract, conjugated linoleic acid (CLA), tetradecyl thioacetic acid (TTA), *Coleus forskohlii* (i.e., forskolin), yohimbine, rauwolscine, capsaicin, raspberry ketones (e.g., 4-(4-hydroxyphenyl) butan-2-one, p-hydroxybenzyl acetone), ephedrine, synephrine (e.g., bitter orange extract), octopamine, 1,3-dimethylamylamine, higenamine, fucoxanthin, acetylcholine modulators and/or adenosine receptor antagonists (e.g., caffeine), nicotine, coca leaves (e.g., teas, extracts, isolates, salts, and free bases), ursolic acid, clenbuterol, noradrenaline reuptake inhibitors (e.g., hordenine, atomoxetine), 7-oxodehydroepiandrosterone (i.e., 7-keto DHEA), thyroid hormones (e.g., triiodothyronine), and combinations thereof.

In another example, a combination supplement may include a beta-hydroxybutyrate component and a component intended to enhance mental alertness, cognition, and/or mood (referred to herein as a "nootropic" component). As with the fat burner embodiments, it is expected that synergistic nootropic effects are greater when the beta-hydroxybutyrate component is a racemic or near mixture rather than more highly enriched in either R-beta-hydroxybutyrate or S-beta-hydroxybutyrate.

Exemplary compounds that may be included in the nootropic component include catecholamine precursors such as tyrosine, L-DOPA (i.e., L-3,4-dihydroxyphenylalanine), tryptophan, and 5-hydroxytryptophan (5-HTP), racetams such as such as piracetam, oxiracetam, and aniracetam, L-theanine, D-serine, phosphatidylserine, tolcapone, uridine, vinpocetine, norepinephrine reuptake inhibitors such as hordenine and atomoxetine, *Panax ginseng*, *Ginkgo biloba*, *Rhodiola rosea*, *Polygala tenuifolia*, *Muira puama*, *Eschscholzia californica*, *Convolvulus pluricaulis*, *Centella asiatica*, *Evolvulus alsinoides*, *Bacopa monnieri*, *Epimedium* herbs, *Ashwagandha* herbs, cyclic adenosine monophosphate (cAMP) modulators such as forskolin, stimulants such as nicotine, caffeine, and amphetamines, cholinergic compounds and/or acetylcholine modulators such as huperzine-A, dimethylaminoethanol, choline, and alpha-glycerophosphocholine, and combinations thereof.

Combination supplements utilizing a racemic or near racemic R,S-beta-hydroxybutyrate component may include other supplements/drugs in addition to or as an alternative to the fat burner component. For example, a combination supplement may include one or more compounds intended to aid in one or more of appetite suppression, weight loss, reduced blood glucose level, improved mental alertness, increased physical energy, improved cognitive function, reduction in traumatic brain injury, reduction in effect of diabetes, improvement of neurological disorder, reduction of cancer, reduction of inflammation, anti-aging, antiglycation, reduction in epileptic seizure, improved mood, increased strength, increased muscle mass, or improved body composition.

In some embodiments, the ketogenic compositions can include or be administered together with other vitamin and/or mineral supplements, such as vitamin $D_3$, and supplements for glucose control, such as berberine and other glucose lowering substances. It is postulated that a racemic or near racemic mixture of R- and S-beta-hydroxybutyrate mixed salt-acid components can provide a longer lasting glucose lowering effect along with other substances.

V. Administration

In some embodiments, the compositions disclosed herein can be used in a method for increasing ketone body level, including promoting and/or sustaining ketosis, in a subject comprising administering to a subject in need thereof a nutritionally or pharmaceutically effective amount of one or more compositions disclosed herein. Examples of beneficial effects of increasing ketone body level, including promoting and/or sustaining ketosis, in a subject include one or more of appetite suppression, weight loss, fat loss, reduced blood glucose level, improved mental alertness, increased physical energy, improved cognitive function, reduction in traumatic brain injury, reduction in effect of diabetes, improvement of neurological disorder, reduction of cancer, reduction of inflammation, anti-aging, antiglycation, reduction in epileptic seizure, improved mood, increased strength, increased muscle mass, or improved body composition.

In some embodiments, administering the racemic or near racemic mixture of R-beta-hydroxybutyrate mixed salt-acid components and S-beta-hydroxybutyrate mixed salt-acid components provides one or more of increased endogenous production of R-beta-hydroxybutyrate and acetoacetate; endogenous conversion of the S-beta-hydroxybutyrate components into one or both of R-beta-hydroxybutyrate and acetoacetate; endogenous conversion of the S-beta-hydroxybutyrate components into fatty acids and sterols; prolonged ketosis; metabolism of the S-beta-hydroxybutyrate components independent of conversion to R-beta-hydroxybutyrate and/or acetoacetate; increased fetal development; increased growth years; reduced endogenous production of acetone during ketosis; signaling by the S-beta-hydroxybutyrate that modulates metabolism of R-beta-hydroxybutyrate and glucose; antioxidant activity; and production of acetyl-CoA.

Ketogenic compositions described herein may be administered to a subject in therapeutically effective dosages and/or in frequencies to induce or sustain ketosis. In some embodiments, a single or unit dose will include a total amount of mixed salt-acid beta-hydroxybutyrate components ranging from about 0.5 gram to about 25 grams, or about 0.75 gram to about 20 grams, or about 1 gram to about 15 grams, or about 1.5 grams to about 12 grams.

The term "unit dose" refers to a dosage form that is configured to deliver a specified quantity or dose of composition or component thereof. Example dosage forms include, but are not limited to, tablets, capsules, powders, food products, food additives, beverages (such as flavored, vitamin fortified, or non-alcoholic), beverage additives (such as flavored, vitamin fortified, or non-alcoholic), candies, suckers, pastilles, food supplements, dietetically acceptable sprays (such as flavored mouth spray), injectables (such as an alcohol-free injectable), and suppositories. Such dosage forms may be configured to provide a full unit dose or fraction thereof (e.g., ½, ⅓, or ¼ of a unit dose).

Another dosage form that can be used to provide a unit dose of composition or component thereof is a unit dose measuring device, such as a cup, scoop, syringe, dropper, spoon, spatula, or colonic irrigation device, which is configured to hold therein a measured quantity of composition equaling a full unit dose or fraction thereof (e.g., ½, ⅓, or ¼ of a unit dose). For example, a bulk container, such as a carton, box, can, jar, bag, pouch, bottle, jug, or keg, containing several unit doses of composition (e.g., 5-250 or 10-150 unit doses) can be provided to a user together with a unit dose measuring device that is configured to provide a unit dose, or fraction thereof, of composition or component thereof.

A kit for use in providing a composition as disclosed herein in bulk form, while providing unit doses of the composition, may comprise a bulk container holding therein a quantity of composition and a unit dose measuring device configured to provide a unit dose, or fraction thereof, of composition or component thereof. One or more unit dose measuring devices may be positioned inside the bulk container at the time of sale, attached to the outside of the bulk container, prepackaged with the bulk container within a larger package, or provided by the seller or manufacture for use with one or multiple bulk containers.

The kit may include instructions regarding the size of the unit dose, or fraction thereof, and the manner and frequency of administration. The instructions may be provided on the bulk container, prepackaged with the bulk container, placed on packaging material sold with the bulk container, or otherwise provided by the seller or manufacturer (e.g., on websites, mailers, flyers, product literature, etc.) The instructions for use may include a reference on how to use the unit dose measuring device to properly deliver a unit dose or fraction thereof. The instructions may additionally or alternatively include a reference to common unit dose measuring devices, such as spoons, spatulas, cups, and the like, not provided with the bulk container (e.g., in case the provided unit dose measuring device is lost or misplaced). In such case, a kit may be constructed by the end user when following instructions provided on or with the bulk container, or otherwise provided by the seller regarding the product and how to properly deliver a unit dose of composition, or fraction thereof.

In some embodiments, the ketogenic compositions can include or be administered together with other supplements, such as vitamin $D_3$, vitamins, minerals, nootropics, and others known in the art. Examples of vitamins, minerals and herbal supplements that can be added to the ketogenic compositions include one or more of vitamin A, vitamin C, vitamin E, niacin, vitamin B6, folic acid, 5-MTHF, vitamin B12, iodine, zinc, copper, manganese, chromium, caffeine, theobromine, theacrine, methylliberine, huperzine A, epicatechins, and enzymes.

In some embodiments, the subject preferably follows a ketogenic diet that restricts intake of carbohydrates and protein during the period of administration of the composition. In one example embodiment, the subject may restrict the dietary intake to a ratio of about 65% fat, about 25% protein, and about 10% carbohydrates. The resulting therapeutic ketosis provides a rapid and sustained keto-adaptation as a metabolic therapy for a wide range of metabolic disorders, and provides nutritional support for therapeutic fasting, weight loss, and performance enhancement. As such, the composition is typically administered once per day, twice per day, or three times per day to a subject desiring to promote and/or sustain a state of ketosis.

In a preferred embodiment, ketogenic compositions can be administered in one or more unit doses per day via oral administration in solid and/or powdered form, such as in a powdered mixture (e.g., powder filled gelatin capsules), hard-pressed tablets, or other oral administration route known to those skilled in the art.

Although oral administration is preferred, other administration routes may additionally or alternatively be utilized. For example, some embodiments may be administered as injectables (e.g., subdermal, parenteral, or intravenous). An injectable may include one or more of mannitol, 1,3-butanediol, propylene glycol, water, Ringer's solution, an isotonic sodium chloride solution, or other suitable dispersing or wetting and suspending agents, including synthetic mono- or diglycerides, and fatty acids, including oleic acid or Cremaphor.

Exemplary compositions for rectal administration include suppositories which can contain, for example, a suitable non-irritating excipient, such as cocoa butter, synthetic glyceride esters or polyethylene glycols, which are solid at ordinary temperatures, but liquify, soften, and/or dissolve in the rectal cavity at body temperature to release the supplement.

Exemplary compositions for nasal or pulmonary administration (e.g., aerosol or inhalation provided through heating or via nebulization) include solutions in saline which can contain, for example, benzyl alcohol or other suitable preservatives, absorption promoters to enhance bioavailability, and/or other solubilizing or dispersing agents such as those known in the art.

In some embodiments, multiple doses of the composition are administered over a period of time. The frequency of administration of the composition can vary depending on any of a variety of factors, such as timing of treatment from previous treatments, objectives of the treatment, and the like. The duration of administration of the composition (e.g., the period of time over which the agent is administered), can vary depending on any of a variety of factors, including subject response, desired effect of treatment, etc.

The amount of the composition to be administered can vary according to factors such as the degree of susceptibility of the individual, the age, sex, and weight of the individual, idiosyncratic responses of the individual, and the like. The "therapeutically effective amount" is that amount necessary to promote a therapeutically effective result in vivo (i.e., therapeutic ketosis). In accordance with the present disclosure, a suitable single dose size is a dose that is capable of preventing or alleviating (reducing or eliminating) a symptom in a patient when administered one or more times over a suitable time period.

The amount of composition administered will depend on potency, absorption, distribution, metabolism, and excretion rates of unused ketone bodies, electrolytes, the method of administration, and the particular disorder being treated, as well as other factors known to those of skill in the art. The dose should be sufficient to affect a desirable response, such as a therapeutic or prophylactic response against a particular disorder or condition, taking into account the severity of the condition to be alleviated. The compounds may be administered once, or may be divided and administered over intervals of time. It is to be understood that administration may be adjusted according to individual need and professional judgment of a person administrating or supervising the administration of the compositions.

VI. Examples

The following is a description of exemplary racemic and near racemic mixtures of R-beta-hydroxybutyrate and S-beta-hydroxybutyrate and other ketogenic compositions useful for raising ketone levels in a subject, including inducing and sustaining a ketogenic state in a subject to which they are administered. It should be appreciated that the beta-hydroxybutyrate compounds described in the examples can be in the form of salts, esters, dimers, trimers, oligomers, and polymers, as discussed herein. The important thing from the standpoint of the examples is equivalent or near equivalent enantiomeric percentages or ratios of R-beta-hydroxybutyrate and S-beta-hydroxybutyrate. The compositions can include a blend of R,S-beta-hydroxybutyrate salts and free R,S-beta-hydroxybutyric acid to provide a desired electrolyte balance, taste and/or pharmacokinetic response. In some cases, the compositions can be a blend of salts, acid, and esters to provide a desired electrolyte balance and/or modulation of ketosis. The compositions can also be combined with short, medium, or long chain fatty acids, esters, glycerides, and other supplements as disclosed herein to provide a desired level of elevated ketone bodies and other effects.

Example 1

A racemic R,S-beta-hydroxybutyrate mixed salt-acid composition is prepared by combining one or more R-beta-hydroxybutyrate salt compounds, one or more S-beta-hydroxybutyrate salt compounds, R-beta-hydroxybutyric acid, and S-beta-hydroxybutyric acid to provide 50% by enantiomeric equivalents of R-beta-hydroxybutyrate mixed salt-acid components and 50% by enantiomeric equivalents of S-beta-hydroxybutyrate mixed salt-acid components. The racemic R,S-beta-hydroxybutyrate mixed salt-acid composition contains less than 100% by molar equivalents of racemic R,S-beta-hydroxybutyrate salts and greater than 0% by molar equivalents of free racemic R,S-beta-hydroxybutyric acids.

Because the racemic mixture includes 50% by enantiomeric equivalents of R-beta-hydroxybutyrate mixed salt-acid compounds, the onset of ketosis is accelerated for a given dosage as compared to the same dosage enriched with S-beta-hydroxybutyrate compounds. On the other hand, because the racemic mixture includes 50% by enantiomeric equivalents of S-beta-hydroxybutyrate mixed salt-acid compounds, the duration of sustained ketosis is increased for a given dosage as compared to the same dosage enriched with R-beta-hydroxybutyrate compounds.

The racemic R,S-beta-hydroxybutyrate mixed salt-acid composition is readily administered as a ketogenic composition, such as in powder form as a dietary supplement mixed with food or drink, in the form of one or more capsules or tablets, or in liquid form such as a mouth spray.

Example 2

The racemic R,S-beta-hydroxybutyrate mixed salt-acid composition of Example 1 is formulated to provide up to 99.9%, 99.8%, 99.7%, 99.6%, 99.5%, 99.4%, 99.3%, 99.2%, 99.1%, 99%, 98.8%, 98.65%, 98.5%, 98.35%, 98.2%, 98%, 97.75%, 97.5%, 97.25%, or 97%, and at least 75%, 80%, 85%, 90%, 92%, 94%, 95%, 96%, or 97%, by molar equivalents of racemic R,S-beta-hydroxybutyrate salts and at least 0.1%, 0.2%, 0.3%, 0.4%, 0.5%, 0.6%, 0.7%, 0.8%, 0.9%, 1%, 1.2%, 1.35%, 1.5%, 1.65%, 1.8%, 2%, 2.25%, 2.5%, 2.75%, or 3%, and less than 25%, 20%, 15%, 10%, 8%, 6%, 5%, 4%, or 3%, by molar equivalents of free racemic R,S-beta-hydroxybutyric acids.

The racemic R,S-beta-hydroxybutyrate mixed salt-acid composition is readily administered as a ketogenic composition, such as in powder form as a dietary supplement mixed with food or drink, in the form of one or more capsules or tablets, or in liquid form such as a mouth spray.

Example 3

Example 1 or Example 2 is modified by combining the racemic R,S-beta-hydroxybutyrate mixed salt-acid composition with a dietetically (i.e., nutritionally) or pharmaceutically acceptable carrier.

Example 4

Any of the foregoing examples is modified by combining the racemic R,S-beta-hydroxybutyrate mixed salt-acid composition with one or more short chain fatty acids, and/or one or more mono-, di- or triglycerides thereof, such as tributyrin.

Example 5

Any of the foregoing examples is modified by combining the racemic R,S-beta-hydroxybutyrate mixed salt-acid composition with one or more medium chain fatty acids, and/or one or more mono-, di- or triglycerides thereof, such as MCT oil.

Example 6

Any of the foregoing examples is modified by combining the racemic R,S-beta-hydroxybutyrate mixed salt-acid composition with one or more long chain fatty acids, and/or one or more mono-, di- or triglycerides thereof.

Example 7

Any of the foregoing examples is modified by combining the racemic R,S-beta-hydroxybutyrate mixed salt-acid composition with one or more supplements, such as vitamin $D_3$, vitamins, minerals, and others known in the art.

Example 8

Any of the foregoing examples is modified by combining the racemic R,S-beta-hydroxybutyrate mixed salt-acid composition with one or more fat burner supplements such as green tea, green tea extract (e.g., a composition including one or more isolated green tea catechins such as epigallocatechin gallate (EGCG)), green coffee extract, conjugated linoleic acid (CLA), tetradecyl thioacetic acid (TTA), Coleus forskohlii (i.e., forskolin), yohimbine, rauwolscine, capsaicin, raspberry ketones (e.g., 4-(4-hydroxyphenyl) butan-2-one, p-hydroxybenzyl acetone), ephedrine, synephrine (e.g., bitter orange extract), octopamine, 1,3-dimethylamylamine, higenamine, fucoxanthin, acetylcholine modulators and/or adenosine receptor antagonists (e.g., caffeine), nicotine, coca leaf derivative, ursolic acid, clenbuterol, noradrenaline reuptake inhibitors (e.g., hordenine, atomoxetine), 7-oxodehydroepiandrosterone (i.e., 7-keto DHEA), thyroid hormones (e.g., triiodothyronine), and combinations thereof.

The resulting combined supplement is expected to provide greater lipolysis and/or fat oxidation effects than a similar dose utilizing a beta-hydroxybutyrate component enriched in R-beta-hydroxybutyrate or enriched in S-beta-hydroxybutyrate.

Example 9

Any of the foregoing examples is modified by combining the racemic R,S-beta-hydroxybutyrate mixed salt-acid composition with one or more nootropic supplements such as tyrosine, L-DOPA (i.e., L-3,4-dihydroxyphenylalanine), tryptophan, and 5-hydroxytryptophan (5-HTP), racetams such as such as piracetam, oxiracetam, and aniracetam, L-theanine, D-serine, phosphatidylserine, tolcapone, uridine, vinpocetine, norepinephrine reuptake inhibitors such as hordenine and atomoxetine, *Panax ginseng*, *Ginkgo biloba*, *Rhodiola rosea*, *Polygala tenuifolia*, *Muira puama*, *Eschscholzia californica*, *Convolvulus pluricaulis*, *Centella asiatica*, *Evolvulus alsinoides*, *Bacopa monnieri*, *Epimedium* herbs, *Ashwagandha* herbs, cyclic adenosine monophosphate (cAMP) modulators such as forskolin, stimulants such as nicotine, caffeine, and amphetamines, cholinergic compounds and/or acetylcholine modulators such as huperzine-A, dimethylaminoethanol, choline, and alpha-glycerophosphocholine, and combinations thereof.

The resulting combined supplement is expected to provide greater cognition, alertness, and/or mood effects than a similar dose utilizing a beta-hydroxybutyrate component enriched in R-beta-hydroxybutyrate or enriched in S-beta-hydroxybutyrate.

Example 10

Any of the foregoing examples is modified by substituting a racemic mixture of R,S-beta-hydroxybutyrate compounds with near racemic mixtures of the R,S-beta-hydroxybutyrate compounds. A near racemic R,S-beta-hydroxybutyrate mixed salt-acid composition includes: (1) from about 48%, 48.5%, 49%, 49.5%, or 49.8% and less than 50% by enantiomeric equivalents of one or more salts of one of R- or S-beta-hydroxybutyrate and greater than 50% and up to about 52%, 51.5%, 51%, 50.5%, or 50.2% by enantiomeric equivalents of one or more salts of the other one of R- or S-beta-hydroxybutyrate and (2) at least 48%, 48.5%, 49%, 49.5%, or 49.8% and less than 50% by enantiomeric equivalents of one of R- or S-beta-hydroxybutyric acid and greater than 50% and up to about 52%, 51.5%, 51%, 50.5%, or 50.2% by enantiomeric equivalents of the other one of R- or S-beta-hydroxybutyric acid.

Example 11

Any of the foregoing examples is modified by including a racemic or near racemic mixture of one or more R,S-beta-hydroxybutyrate esters. A racemic mixture contains enantiomerically equivalent amounts of R- and S-beta-hydroxybutyrate esters. A near racemic mixture contains nonequivalent amounts of R- and S-beta-hydroxybutyrate esters, such from about 48%, 48.5%, 49%, 49.5%, or 49.8% and less than 50% by enantiomeric equivalents of one or more esters of one of R- or S-beta-hydroxybutyrate and up to about 52%, 51.5%, 51%, 50.5%, or 50.2% by enantiomeric equivalents of one or more esters of the other one of R- or S-beta-hydroxybutyrate.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A racemic or near racemic R,S-beta-hydroxybutyrate mixed salt-acid composition for increasing ketone level in a subject, comprising:

a racemic mixture of beta-hydroxybutyric acids containing 50% by enantiomeric equivalents of R-beta-hydroxybutyric acid and 50% by enantiomeric equivalents of S-beta-hydroxybutyric acid or a near racemic mixture of beta-hydroxybutyric acids containing at least 48% and less than 50% by enantiomeric equivalents of one of R- or S-beta-hydroxybutyric acid and greater than 50% and up to 52% by enantiomeric equivalents of another one of R- or S-beta-hydroxybutyric acid; and a racemic mixture of beta-hydroxybutyrate salts containing 50% by enantiomeric equivalents of one or more R-beta-hydroxybutyrate salts and 50% by enantiomeric equivalents of one or more S-beta-hydroxybutyrate salts or a near racemic mixture of beta-hydroxybutyrate salts containing at least 48% and less than 50% by enantiomeric equivalents of one or more salts of R- or S-beta-hydroxybutyrate and greater than 50% and up to 52% by enantiomeric equivalents of one or more salts of another one of R- or S-beta-hydroxybutyrate, wherein the composition comprises 75% to 99.9% by molar equivalents of the racemic or near racemic mixture of R- and S-beta-hydroxybutyrate salts and 25% to 0.1% by molar equivalents of the racemic or near racemic mixture of R- and S-beta-hydroxybutyric acids, wherein the beta-hydroxybutyrate salts include:
  at least two salts are selected from the group consisting of sodium R-beta-hydroxybutyrate; potassium R-beta-hydroxybutyrate; calcium R-beta-hydroxybutyrate; and magnesium R-beta-hydroxybutyrate; and
  at least two salts selected from the group consisting of sodium S-beta-hydroxybutyrate; potassium S-beta-hydroxybutyrate; calcium S-beta-hydroxybutyrate; and magnesium S-beta-hydroxybutyrate,
  wherein the mixed salt-acid composition is in solid and/or powder form.

2. The mixed salt-acid composition of claim 1, wherein the composition comprises at least two of:
  a racemic or near racemic mixture of sodium R-beta-hydroxybutyrate and sodium S-beta-hydroxybutyrate;
  a racemic or near racemic mixture of potassium R-beta-hydroxybutyrate and potassium S-beta-hydroxybutyrate;
  a racemic or near racemic mixture of calcium R-beta-hydroxybutyrate and calcium S-beta-hydroxybutyrate; or
  a racemic or near racemic mixture of magnesium R-beta-hydroxybutyrate and magnesium S-beta-hydroxybutyrate.

3. The mixed salt-acid composition of claim 1, wherein the composition comprises:
  a near racemic mixture of beta-hydroxybutyric acids containing from about 48.5% to less than 50% by enantiomeric equivalents of one of R- or S-beta-hydroxybutyric acid and greater than 50% and up to about 51.5% by enantiomeric equivalents of another one of R- or S-beta-hydroxybutyric acid; and
  a near racemic mixture of beta-hydroxybutyrate salts containing at least 48.5% and less than 50% by enantiomeric equivalents of one or more salts of R- or S-beta-hydroxybutyrate and greater than 50% and up to 51.5% by enantiomeric equivalents of one or more salts of another one of R- or S-beta-hydroxybutyrate.

4. The mixed salt-acid composition of claim 1, wherein the composition comprises:
  a near racemic mixture of beta-hydroxybutyric acids containing from about 49% to less than 50% by enantiomeric equivalents of one of R- or S-beta-hydroxybutyric acid and greater than 50% and up to about 51% by enantiomeric equivalents of another one of R- or S-beta-hydroxybutyric acid; and
  a near racemic mixture of beta-hydroxybutyrate salts containing at least 49% and less than 50% by enantiomeric equivalents of one or more salts of R- or S-beta-hydroxybutyrate and greater than 50% and up to 51% by enantiomeric equivalents of one or more salts of another one of R- or S-beta-hydroxybutyrate.

5. The mixed salt-acid composition of claim 1, wherein the composition comprises:
  a near racemic mixture of beta-hydroxybutyric acids containing from about 49.5% to less than 50% by enantiomeric equivalents of one of R- or S-beta-hydroxybutyric acid and greater than 50% and up to about 50.5% by enantiomeric equivalents of another one of R- or S-beta-hydroxybutyric acid; and
  a near racemic mixture of beta-hydroxybutyrate salts containing at least 49.5% and less than 50% by enantiomeric equivalents of one or more salts of R- or S-beta-hydroxybutyrate and greater than 50% and up to 50.5% by enantiomeric equivalents of one or more salts of another one of R- or S-beta-hydroxybutyrate.

6. The mixed salt-acid composition of claim 1, wherein the composition comprises:
  a near racemic mixture of beta-hydroxybutyric acids containing from about 49.8% to less than 50% by enantiomeric equivalents of one of R- or S-beta-hydroxybutyric acid and greater than 50% and up to about 50.2% by enantiomeric equivalents of another one of R- or S-beta-hydroxybutyric acid; and
  a near racemic mixture of beta-hydroxybutyrate salts containing at least 49.8% and less than 50% by enantiomeric equivalents of one or more salts of R- or S-beta-hydroxybutyrate and greater than 50% and up to 50.2% by enantiomeric equivalents of one or more salts of another one of R- or S-beta-hydroxybutyrate.

7. The mixed salt-acid composition of claim 1, further comprising at least one short chain fatty acid having less than 6 carbons, or a mono-, di- or triglyceride of the at least one short chain fatty acid.

8. The mixed salt-acid composition of claim 1, further comprising at least one of:
  a fat burner supplement for increasing lipolysis and/or fat oxidation; or
  a nootropic supplement for increasing cognitive performance, alertness, and/or mood.

9. The mixed salt-acid composition of claim 8, wherein the one or more fat burner supplements are selected from the group consisting of green tea, green tea extract, isolated green tea catechins, epigallocatechin gallate (EGCG), green coffee extract, conjugated linoleic acid (CLA), tetradecyl thioacetic acid (TTA), *Coleus forskohlii*, yohimbine, rauwolscine, capsaicin, raspberry ketones, 4-(4-hydroxyphenyl) butan-2-one, p-hydroxybenzyl acetone, ephedrine, synephrine, octopamine, 1,3-dimethylamyl-amine, higenamine, fucoxanthin, acetylcholine modulators and/or adenosine receptor antagonists, caffeine, nicotine, coca leaf derivatives, ursolic acid, clenbuterol, noradrenaline reuptake inhibitors, hordenine, atomoxetine, 7-oxodehydroepiandrosterone, triiodothyronine, and combinations thereof.

10. The mixed salt-acid composition of claim 8, wherein the one or more nootropic compounds are selected from the group consisting of tyrosine, L-DOPA, tryptophan, 5-hydroxytryptophan, racetams, piracetam, oxiracetam, aniracetam, L-theanine, D-serine, phosphatidylserine, tolcapone, uridine, vinpocetine, norepinephrine reuptake inhibitors, hordenine, atomoxetine, *Panax ginseng, Ginkgo biloba, Rhodiola rosea, Polygala tenuifolia, Muira puama, Eschscholzia, californica, Convolvulus pluricaulis, Centella asiatica, Evolvulus alsinoides, Bacopa monnieri, Epimedium* herbs, *Ashwagandha* herbs, cyclic adenosine monophosphate (cAMP) modulators, forskolin, nicotine, caffeine, amphetamines, coca leaf derivatives, cholinergic compounds, acetylcholine modulators, huperzine-A, dimethylaminoethanol, choline, alpha-glycerophosphocholine, and combinations thereof.

11. The mixed salt-acid composition of claim 1, further comprising a racemic or near racemic mixture of one or more R-beta-hydroxybutyrate esters and one or more S-beta-hydroxybutyrate esters.

12. A kit for administering ketone bodies to a subject, comprising:
  the racemic or near racemic R,S-beta-hydroxybutyrate mixed salt-acid composition of claim 1;
  a container in which the mixed salt-acid composition is placed; and
  a measuring device configured to hold therein a unit dose, or fraction thereof, of the mixed salt-acid composition, wherein a unit dose of the composition contains about 0.5 g to about 25 g of beta-hydroxybutyrate compounds.

13. The kit of claim 12, wherein the container is selected from the group consisting of carton, box, can, jar, bag, pouch, bottle, jug, and keg.

14. The kit of claim 12, wherein the measuring device is selected from the group consisting of cup, scoop, syringe, dropper, spatula, spoon, and colonic irrigation device.

15. A racemic or near racemic R,S-beta-hydroxybutyrate mixed salt-acid composition for increasing ketone level in a subject, comprising:
   a racemic mixture of beta-hydroxybutyric acids containing 50% by enantiomeric equivalents of R-beta-hydroxybutyric acid and 50% by enantiomeric equivalents of S-beta-hydroxybutyric acid or a near racemic mixture of beta-hydroxybutyric acids containing at least 48% and less than 50% by enantiomeric equivalents of one of R- or S-beta-hydroxybutyric acid and greater than 50% and up to 52% by enantiomeric equivalents of another one of R- or S-beta-hydroxybutyric acid; and
   a racemic mixture of beta-hydroxybutyrate salts containing 50% by enantiomeric equivalents of one or more R-beta-hydroxybutyrate salts and 50% by enantiomeric equivalents of one or more S-beta-hydroxybutyrate salts or a near racemic mixture of beta-hydroxybutyrate salts containing at least 48% and less than 50% by enantiomeric equivalents of one or more salts of R- or S-beta-hydroxybutyrate and greater than 50% and up to 52% by enantiomeric equivalents of one or more salts of another one of R- or S-beta-hydroxybutyrate,
   wherein the composition comprises 75% to 99.9% by molar equivalents of the racemic or near racemic mixture of beta-hydroxybutyrate salts and 25% to 0.1% by molar equivalents of the racemic or near racemic mixture of beta-hydroxybutyric acids,
   wherein the beta-hydroxybutyrate salts include:
      at least one salt selected from the group consisting of sodium R-beta-hydroxybutyrate; potassium R-beta-hydroxybutyrate; calcium R-beta-hydroxybutyrate; and magnesium R-beta-hydroxybutyrate; and
      at least one salt—selected from the group consisting of sodium S-beta-hydroxybutyrate; potassium S-beta-hydroxybutyrate; calcium S-beta-hydroxybutyrate; and magnesium S-beta-hydroxybutyrate;
   wherein the composition is provided as or in a tablet, capsule, powder, food product, food additive, flavored beverage, vitamin fortified beverage, non-alcoholic beverage, flavored beverage additive, vitamin fortified beverage additive, non-alcoholic beverage additive, candy, sucker, pastille, food supplement, flavored mouth spray, or suppository.

16. The mixed salt-acid composition of claim 15, wherein the composition comprises:
   a near racemic mixture of beta-hydroxybutyric acids containing from about 49% to less than 50% by enantiomeric equivalents of one of R- or S-beta-hydroxybutyric acid and greater than 50% and up to about 51% by enantiomeric equivalents of another one of R- or S-beta-hydroxybutyric acid; and
   a near racemic mixture of beta-hydroxybutyric salts containing at least 49% and less than 50% by enantiomeric equivalents of one or more salts of R- or S-beta-hydroxybutyrate and greater than 50% and up to 51% by enantiomeric equivalents of one or more salts of another one of R- or S-beta-hydroxybutyrate.

17. The mixed salt-acid composition of claim 15, wherein the composition comprises:
   a near racemic mixture of beta-hydroxybutyric acids containing from about 49.5% to less than 50% by enantiomeric equivalents of one of R- or S-beta-hydroxybutyric acid and greater than 50% and up to about 50.5% by enantiomeric equivalents of another one of R- or S-beta-hydroxybutyric acid; and
   a near racemic mixture of beta-hydroxybutyric salts containing at least 49.5% and less than 50% by enantiomeric equivalents of one or more salts of R- or S-beta-hydroxybutyrate and greater than 50% and up to 50.5% by enantiomeric equivalents of one or more salts of another one of R- or S-beta-hydroxybutyrate.

18. A racemic or near racemic R,S-beta-hydroxybutyrate mixed salt-acid composition for increasing ketone level in a subject, comprising:
   a dietetically or pharmaceutically acceptable carrier selected from the group consisting of tablet, capsule, powder, food product, food additive, flavored beverage, vitamin fortified beverage, non-alcoholic beverage, flavored beverage additive, vitamin fortified beverage additive, non-alcoholic beverage additive, candy, sucker, pastille, food supplement, flavored mouth spray, and suppository;
   a racemic mixture of beta-hydroxybutyric acids containing 50% by enantiomeric equivalents of R-beta-hydroxybutyric acid and 50% by enantiomeric equivalents of S-beta-hydroxybutyric acid or a near racemic mixture of beta-hydroxybutyric acids containing at least 48% and less than 50% by enantiomeric equivalents of one of R- or S-beta-hydroxybutyric acid and greater than 50% and up to 52% by enantiomeric equivalents of another one of R- or S-beta-hydroxybutyric acid; and
   a racemic mixture of beta-hydroxybutyrate salts containing 50% by enantiomeric equivalents of one or more R-beta-hydroxybutyrate salts and 50% by enantiomeric equivalents of one or more S-beta-hydroxybutyrate salts or a near racemic mixture of beta-hydroxybutyrate salts containing at least 48% and less than 50% by enantiomeric equivalents of one or more salts of R- or S-beta-hydroxybutyrate and greater than 50% and up to 52% by enantiomeric equivalents of one or more salts of another one of R- or S-beta-hydroxybutyrate,
   wherein the composition comprises 75% to 99.9% by molar equivalents of the racemic or near racemic mixture of beta-hydroxybutyrate salts and 25% to 0.1% by molar equivalents of the racemic or near racemic mixture of beta-hydroxybutyric acids,
   wherein the beta-hydroxybutyrate salts include:
      at least one salt mixture selected from calcium R-beta-hydroxybutyrate and calcium S-beta-hydroxybutyrate or magnesium R-beta-hydroxybutyrate and magnesium S-beta-hydroxybutyrate; and
      at least one other salt mixture selected from the group consisting of: sodium R-beta-hydroxybutyrate and sodium S-beta-hydroxybutyrate; potassium R-beta-hydroxybutyrate and potassium S-beta-hydroxybutyrate; calcium R-beta-hydroxybutyrate and calcium S-beta-hydroxybutyrate; and magnesium R-beta-hydroxybutyrate and magnesium S-beta-hydroxybutyrate.

19. The mixed salt-acid composition of claim 18, wherein the composition comprises:
   a near racemic mixture of beta-hydroxybutyric acids containing from about 49% to less than 50% by enantiomeric equivalents of one of R- or S-beta-hydroxybutyric acid and greater than 50% and up to about 51% by enantiomeric equivalents of another one of R- or S-beta-hydroxybutyric acid; and a near racemic mixture of beta-hydroxybutyric salts containing at least 49% and less than 50% by enantiomeric equivalents of one or more salts of R- or S-beta-hydroxybutyrate and greater than 50% and up to 51% by enantiomeric equivalents of one or more salts of another one of R- or S-beta-hydroxybutyrate.

20. The mixed salt-acid composition of claim 18, wherein the composition comprises:

a near racemic mixture of beta-hydroxybutyric acids containing from about 49.5% to less than 50% by enantiomeric equivalents of one of R- or S-beta-hydroxybutyric acid and greater than 50% and up to about 50.5% by enantiomeric equivalents of another one of R- or S-beta-hydroxybutyric acid; and a near racemic mixture of beta-hydroxybutyric salts containing at least 49.5% and less than 50% by enantiomeric equivalents of one or more salts of R- or S-beta-hydroxybutyrate and greater than 50% and up to 50.5% by enantiomeric equivalents of one or more salts of another one of R- or S-beta-hydroxybutyrate.

* * * * *